(12) United States Patent
Kamal et al.

(10) Patent No.: US 8,927,538 B2
(45) Date of Patent: Jan. 6, 2015

(54) CARBAZOLE LINKED PYRROLO[2,1-C][1,4]BENZODIAZEFINE HYBRIDS AS POTENTIAL ANTICANCER AGENTS AND PROCESS FOR THE PREPARATION THEREOF

(75) Inventors: Ahmed Kamal, Hyderabad (IN); Rajesh V. C. R. N. C Shetti, Hyderabad (IN); Srinivasa K. Reddy, Hyderabad (IN); Adla Malla Reddy, Hyderabad (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 13/129,465

(22) PCT Filed: Dec. 3, 2010

(86) PCT No.: PCT/IB2010/003087
§ 371 (c)(1),
(2), (4) Date: Dec. 22, 2011

(87) PCT Pub. No.: WO2011/117668
PCT Pub. Date: Sep. 29, 2011

(65) Prior Publication Data
US 2013/0131336 A1    May 23, 2013

(30) Foreign Application Priority Data

Mar. 22, 2010   (IN) .............................. 678/DEL/2010

(51) Int. Cl.
*C07D 487/04*    (2006.01)

(52) U.S. Cl.
CPC ................... *C07D 487/04* (2013.01)
USPC .......................................... 514/220; 540/497

(58) Field of Classification Search
None
See application file for complete search history.

(56) References Cited

FOREIGN PATENT DOCUMENTS

WO    2006003670    1/2006

OTHER PUBLICATIONS

M.Tercel, et al; Unsymmetrical DNA Cross-Linking Agents: Combination of the CBI and PBD Pharmacophores; J. Med.Chem; vol. No. 46, 2003, pp. 2132-2151.
L.A. Masterson, et al; Synthesis and Biological evaluation of pyrrolo[2,1-c][1,4]benzodiazepine (PBD) C8 cyclic amine conjugates; Bioorganic & Medicinal Chemistry Letters; vol. 14, 2004, pp. 901-904.

*Primary Examiner* — Noble Jarrell
(74) *Attorney, Agent, or Firm* — Cowan, Liebowitz & Latman, P.C.; Mark Montague

(57) ABSTRACT

The present invention provides a compound of general formulae A useful as potential antitumour agents against human cancer cell lines. The present invention further provides a process for the preparation of pyrrolo[2, 1-c][1,4]benzodiazepine hybrids of general formulae 6a-g, 10a-o, 14a-g and 18a-o.

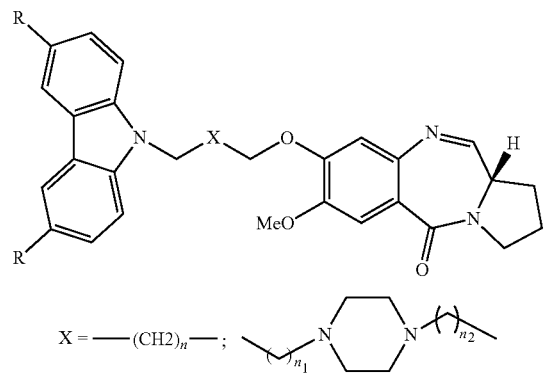

Formula A $X = -(CH_2)_n-$;

$n = 1-7$; $n_1, n_2 = 2-6$
R = H, Ph, 4-OMe(Ph), 4-OCF$_3$—(Ph), 4-F(Ph), 4-Cl(Ph)

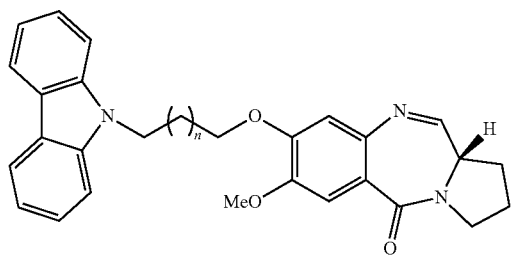

Formula-6a-g $n = 1-7$

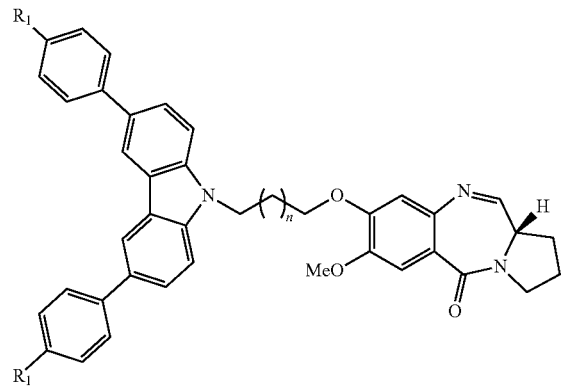

Formula-10a-o $n = 1-3$
$R_1$ = H, OMe, OCF$_3$, F, Cl

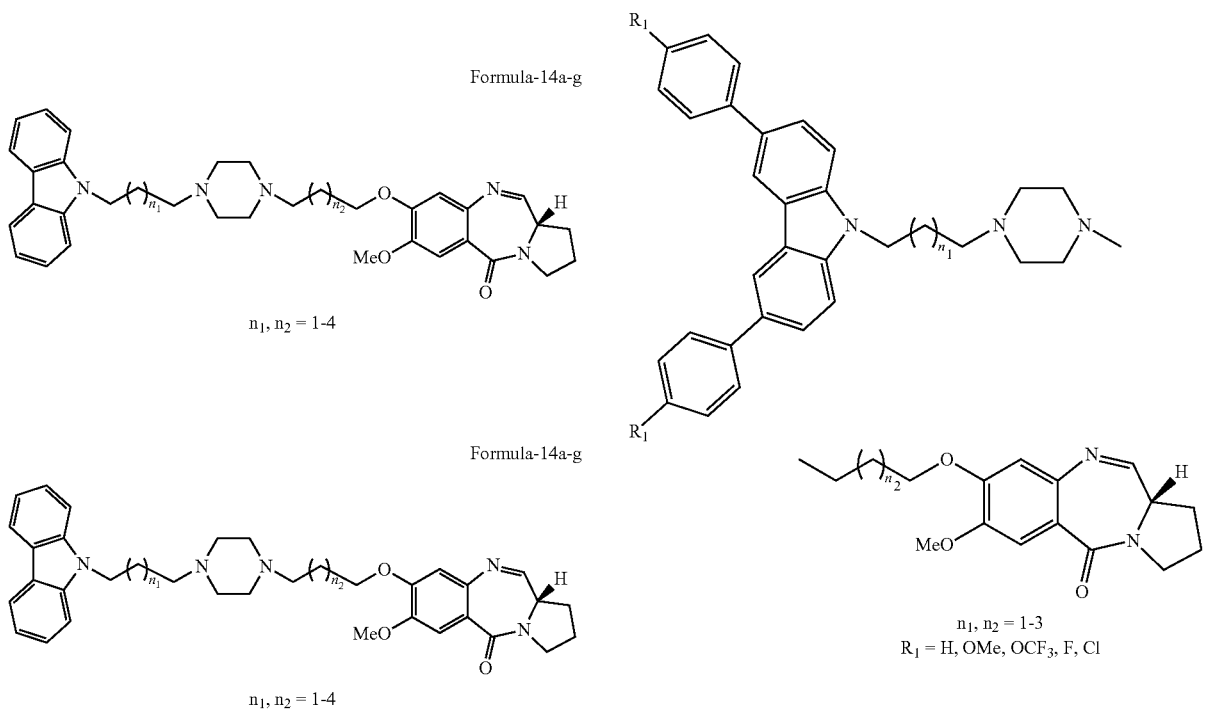
26 Claims, No Drawings

CARBAZOLE LINKED PYRROLO[2,1-C][1,4]BENZODIAZEPINE HYBRIDS AS POTENTIAL ANTICANCER AGENTS AND PROCESS FOR THE PREPARATION THEREOF

FIELD OF THE INVENTION

The present invention relates to carbazole linked pyrrolo [2,1-c][1,4]benzodiazepine hybrids of general formula A as anticancer agents. More particularly, the present invention relates to a process for the preparation of carbazole linked pyrrolo[2,1-c][1,4]benzodiazepine hybrids of general formula A.

Formula A

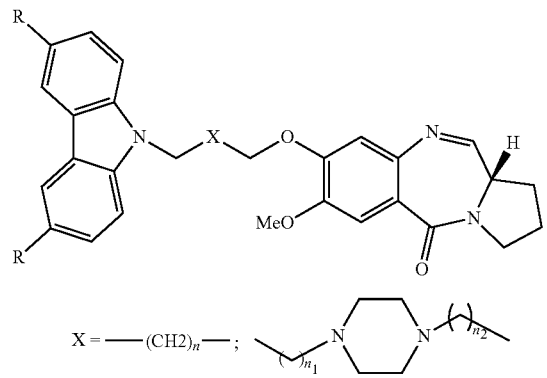

$X = ----(CH2)_n----$ ;

$n = 1-7; n_1, n_2 = 2-6$

R = H, Ph, 4-OMe(Ph), 4-OCF$_3$----(Ph), 4-F(Ph), 4-Cl(Ph)

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665; Kohn, K. W. and Speous, C. L. *J. Mol. Biol.*, 1970, 51, 551; Hurley, L. H.; Gairpla, C. and Zmijewski, M. *Biochem. Biophys. Acta.*, 1977, 475, 521; Kaplan, D. J. and Hurley, L. H. *Biochemistry*, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S, and Hurley, L. H. *J. Org. Chem.* 1996, 61, 8141).

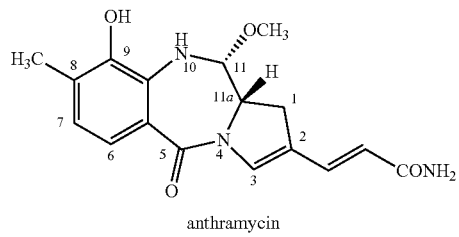

anthramycin

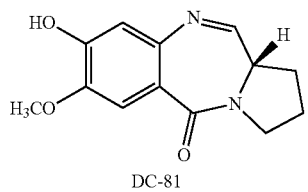

DC-81

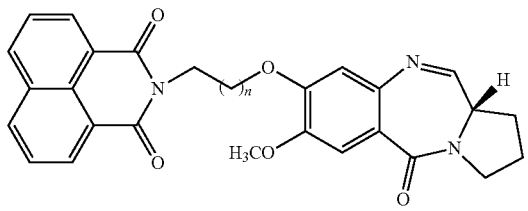

n = 1-9
Napthalimide-PBD hydbrid

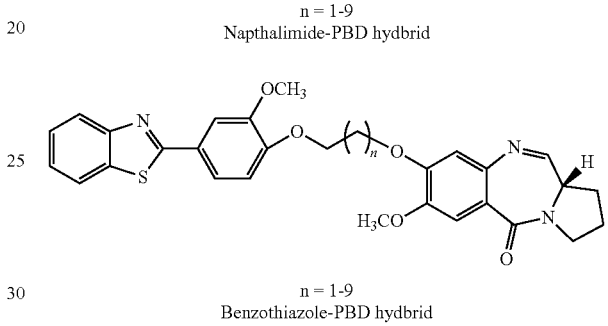

n = 1-9
Benzothiazole-PBD hydbrid

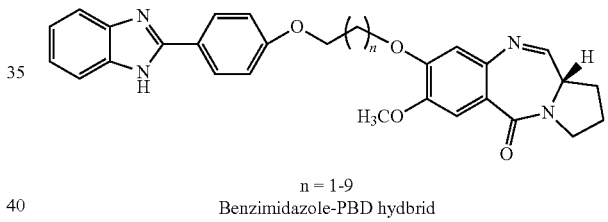

n = 1-9
Benzimidazole-PBD hydbrid

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). Recently, some new pyrrolobenzodiazepine (PBD) hybrids have been synthesized that have significant DNA binding ability and potent antitumour activity. (Kamal, A.; Srinivas, O.; Ramulu, P.; Ramesh, G.; Kumar, P. P. *Bioorg. Med. Chem. Lett.* 2003, 13, 3577).

Naturally occurring pyrrolo[2,1-c][1,4]benzodiazepines belong to a group of antitumour antibiotics derived from *Streptomyces* species. Recently, there is much impetus for the PBD systems as they can recognize and bind to specific sequence of DNA. Examples of naturally occurring PBDs include anthramycin, DC-81, tomaymycin, sibiromycin and neothramycin. However, the clinical efficacy for these antibiotics is hindered by several limitations, such as poor water solubility, cardiotoxicity, development of drug resistance and metabolic inactivation.

OBJECTIVES OF THE INVENTION

The main objective of the present invention is to provide carbazole linked pyrrolo[2,1-c][1,4]benzodiazepine hybrids.

The another objective of the present invention is to provide carbazole linked pyrrolo[2,1-c][1,4]benzodiazepine hybrids, useful as antitumour agents.

Yet another object of this invention is to provide a process for the preparation of carbazole linked pyrrolo[2,1-c][1,4] benzodiazepine hybrids.

SUMMARY OF THE INVENTION

Accordingly, the present invention provides carbazole linked pyrrolo[2,1-c][1,4]benzodiazepine hybrids of general formulae A.

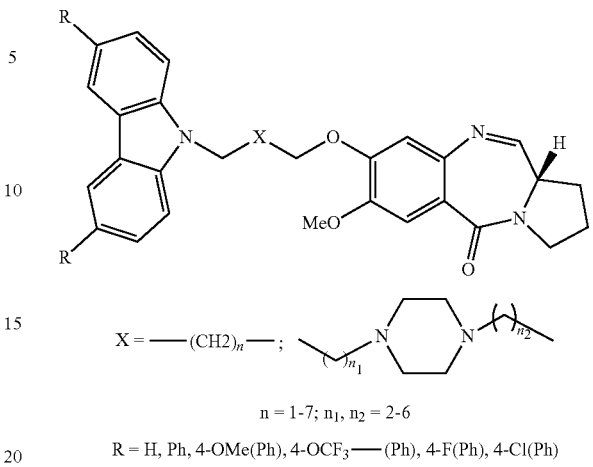

Formula A $X = \text{---}(CH_2)_n\text{---}$;

$n = 1\text{-}7; n_1, n_2 = 2\text{-}6$ $R = H, Ph, 4\text{-}OMe(Ph), 4\text{-}OCF_3\text{---}(Ph), 4\text{-}F(Ph), 4\text{-}Cl(Ph)$ In one embodiment of the present invention, the carbazole linked pyrrolo[2,1-c][1,4]benzodiazepine hybrids of formula A is represented by the compounds of general formulae 6a-g, 10a-o, 14a-g and 18a-o.

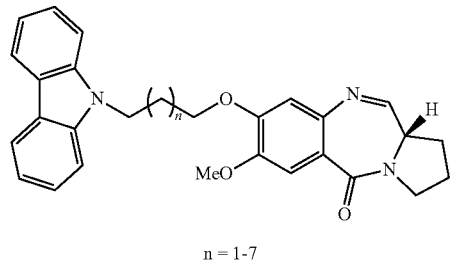

Formula-6a-g $n = 1\text{-}7$

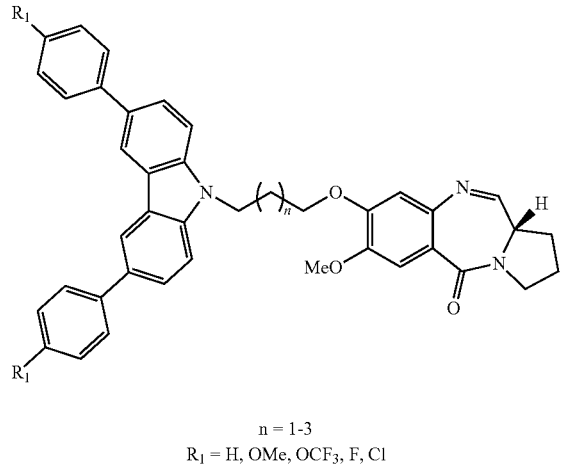

Formula-10a-o $n = 1\text{-}3$
$R_1 = H, OMe, OCF_3, F, Cl$

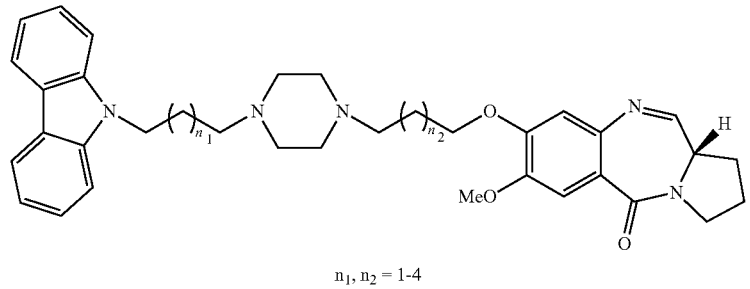

Formula-14a-g $n_1, n_2 = 1\text{-}4$

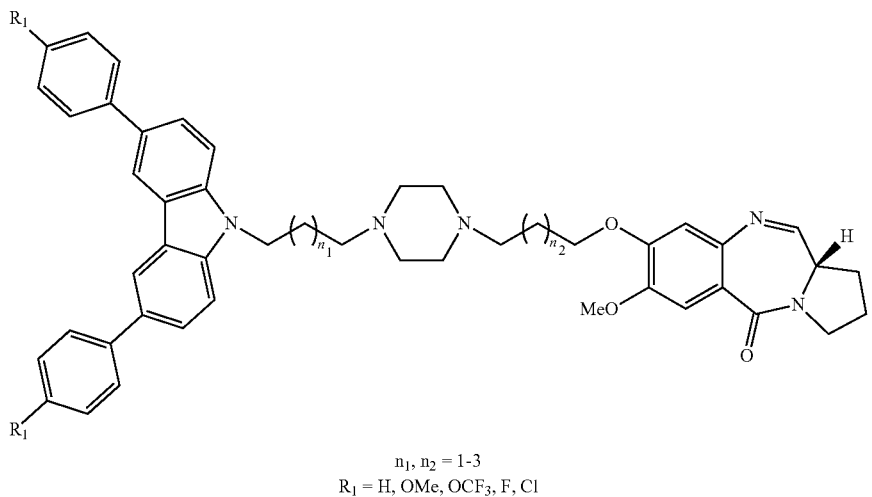

Formula-18a-o $n_1, n_2 = 1-3$
$R_1 = $ H, OMe, OCF$_3$, F, Cl

In another embodiment of the present invention, carbazole linked pyrrolo[2,1-c][1,4]benzodiazepine hybrids is represented, by the group of the following compounds:

7-methoxy-8-[3-(9H-9-carbazoly)propyloxy]-(11aS)-1,2,3,11a-tetrahydro-5H-pyrrolo[2,1-c][1,4]benzodiazepin-5-one 6a, 7-methoxy-8-[4-(9H-9-carbazoly)butyloxy]-(11aS)-1,2,3,11a-tetrahydro-5H-pyrrolo[2,1-c][1,4]benzodiazepin-5-one 6b, 7-methoxy-8-[5-(9H-9-carbazoly)pentyloxy]-(11aS)-1,2,3,11a-tetrahydro-5H-pyrrolo[2,1-c][1,4]benzodiazepin-5-one 6c, 7-methoxy-8-[6-(9H-9-carbazoly)hexyloxy]-(11aS)-1,2,3,11a-tetrahydro-5H-pyrrolo[2,1-c][1,4]benzodiazepin-5-one 6d, 7-methoxy-8-[7-(9H-9-carbazoly)heptyloxy]-(11aS)-1,2,3,11a-tetrahydro-5H-pyrrolo[2,1-c][1,4]benzodiazepin-5-one 6e, 7-methoxy-8-[8-(9H-9-carbazoly)octyloxy]-(11aS)-1,2,3,11a-tetrahydro-5H-pyrrolo[2,1-c][1,4]benzodiazepin-5-one 6f, 7-methoxy-8-[9-(9H-9-carbazoly)nonyloxy]-(11aS)-1,2,3,11a-tetrahydro-5H-pyrrolo[2,1-c][1,4]benzodiazepin-5-one 6g, 7-methoxy-8-{3-[3,6-d]-phenyl-9H-9-carbazoly]propyloxy]}-(11aS)-1,2,3,11a-tetrahydro-5H-pyrrolo[2,1-c][1,4]benzodiazepin-5-one 10a, 7-methoxy-8-{4-[3,6-di-phenyl-9H-9-carbazoly]butyloxyl]}-(11aS)-1,2,3,11a-tetrahydro-5H-pyrrolo[2,1-c][1,4]benzodiazepin-5-one 10b, 7-methoxy-8-{5-[3,6-d]-phenyl-9H-9-carbazoly]pentyloxy}-(11aS)-1,2,3,11a-tetrahydro-5H-pyrrolo[2,1-c][1,4]benzodiazepin-5-one 10c, 7-methoxy-8-{3-[3,6-di(4-methoxyphenyl)-9H-9-carbazoly]propyloxy]}-(11aS)-1,2,3,11a-tetrahydro-5H-pyrrolo[2,1-c][1,4]benzodiazepin-5-one 10d, 7-methoxy-8-{4-[3,6-di(4-methoxyphenyl)-9H-9-carbazoly]butyloxy]}-(11aS)-1,2,3,11a-tetrahydro-5H-pyrrolo[2,1-c][1,4]benzodiazepin-5-one 10e, 7-methoxy-8-{5-[3,6-di(4-methoxyphenyl)-9H-9-carbazoly]pentyloxy}-(11aS)-1,2,3,11a-tetrahydro-5H-pyrrolo[2,1-c][1,4]benzodiazepin-5-one 10f, 7-methoxy-8-{3-[3,6-di(4-trifluoromethoxyphenyl)-9H-9-carbazoly]propyloxy}-(11aS)-1,2,3,11a-tetrahydro-5H-pyrrolo[2,1-c][1,4]benzodiazepin-5-one 10g, 7-methoxy-8-{4-[3,6-di(4-trifluoromethoxyphenyl)-9H-9-carbazoly]butyloxy}-(11aS)-1,2,3,11a-tetrahydro-5H-pyrrolo[2,1-c][1,4]benzodiazepin-5-one 10h, 7-methoxy-8-{5-[3,6-di(4-trifluoromethoxyphenyl)-9H-9-carbazoly]pentyloxy}-(11aS)-1,2,3,11a-tetrahydro-5H-pyrrolo[2,1-c][1,4]benzodiazepin-5-one 10i, 7-methoxy-8-{3-[3,6-di(4-fluorophenyl)-9H-9-carbazoly]propyloxy}-(11aS)-1,2,3,11a-tetrahydro-5H-pyrrolo[2,1-c][1,4]benzodiazepin-5-one 10j, 7-methoxy-8-{4-[3,6-di(4-fluorophenyl)-9H-9-carbazoly]butyloxy}-(11aS)-1,2,3,11a-tetrahydro-5H-pyrrolo[2,1-c][1,4]benzodiazepin-5-one 10k, 7-methoxy-8-{5-[3,6-di(4-fluorophenyl)-9H-9-carbazoly]pentyloxy}-(11aS)-1,2,3,11a-tetrahydro-5H-pyrrolo[2,1-c][1,4]benzodiazepin-5-one 10l, 7-methoxy-8-{3-[3,6-di(4-chlorophenyl)-9H-9-carbazoly]propyloxy}-(11aS)-1,2,3,11a-tetrahydro-5H-pyrrolo[2,1-c][1,4]benzodiazepin-5-one 10m, 7-methoxy-8-{4-[3,6-di(4-chlorophenyl)-9H-9-carbazoly]butyloxy}-(11aS)-1,2,3,11a-tetrahydro-5H-pyrrolo[2,1-c][1,4]benzodiazepin-5-one 10n, 7-methoxy-8-{5-[3,6-di(4-chlorophenyl)-9H-9-carbazoly]pentyloxy}-(11aS)-1,2,3,11a-tetrahydro-5H-pyrrolo[2,1-c][1,4]benzodiazepin-5-one 10o, 7-methoxy-8-(3-{4-[3-(9H-9-carbazoly)propyloxy]piperazino}propyloxy)-(11aS)-1,2,3,11a-tetrahydro-5H-pyrrolo[2,1-c][1,4]benzodiazepin-5-one 14a, 7-methoxy-8-(3-{4-[4-(9H-9-carbazoly)butyloxy]piperazino}propyloxy)-(11aS)-1,2,3,11a-tetrahydro-5H-pyrrolo[2,1-c][1,4]benzodiazepin-5-one 14b, 7-methoxy-8-(4-{4-[3-(9H-9-carbazoly)propyloxy]piperazino}butyloxy)-(11aS)-1,2,3,11a-tetrahydro-5H-pyrrolo[2,1-c][1,4]benzodiazepin-5-one 14c, 7-methoxy-8-(4-{4-[4-(9H-9-carbazoly)butyloxy]piperazino}butyloxy)-(11aS)-1,2,3,11a-tetrahydro-5H-pyrrolo[2,1-c][1,4]benzodiazepin-5-one 14d, 7-methoxy-8-(5-{4-[5-(9H-9-carbazoly)pentyloxy]piperazino}pentyloxy)-(11aS)-1,2,3,11a-tetrahydro-5H-pyrrolo[2,1-c][1,4]benzodiazepin-5-one 14e 7-methoxy-8-(6-{4-[6-(9H-9-carbazoly)hexyloxy]piperazino}hexyloxy)-(11aS)-1,2,3,11a-tetrahydro-5H-pyrrolo[2,1-c][1,4]benzodiazepin-5-one 14f, 7-methoxy-8-(5-{4-[4-(9H-9-carbazoly)butyloxy]piperazino}pentyloxy)-(11aS)-1,2,3,11a-tetrahydro-5H-pyrrolo[2,1-c][1,4]benzodiazepin-5-one 14g, 7-methoxy-8-[3-(4-{3-[3,6-d]-phenyl-9H-9-carbazoly]propyloxy}piperazino)propyloxy]-(11aS)-1,2,3,11a-tetrahydro-5H-pyrrolo[2,1-c][1,4]benzodiazepin-5-one 18a, 7-methoxy-8-[4-(4-{4-[3,6-d]-phenyl-9H-9-carbazoly]butyloxy}piperazino)butyloxy]-(11aS)-1,2,3,11a-tetrahydro-5H-pyrrolo[2,1-c][1,4]benzodiazepin-5-one 18b, 7-methoxy-8-[3-(4-{3-[3,6-di(4-methoxyphenyl)-9H-9-carbazoly]propyloxy}piperazino)proyloxy]-(11aS)-1,2,3,11a-tetrahydro-5H-pyrrolo[2,1-c][1,4]benzodiazepin-5-one 18c, 7-methoxy-8-[3-(4-{4-[3,6-di(4-methoxyphenyl)-9H-9-carbazoly]propyloxy}piperazino)butyloxy]-(11aS)-1,2,3,11a-tetrahydro-5H-pyrrolo[2,1-c][1,4]benzodiazepin-5-one 18d, 7-methoxy-8-[4-(4-{3-[3,6-di(4-methoxyphenyl)-9H-9-carbazoly]butyloxy}piperazino)propyloxy]-(11aS)-1,2,3,11a-tetrahydro-5H-pyrrolo[2,1-c][1,4]benzodiazepin-5-one 18e, 7-methoxy-8-[4-(4-{4-[3,6-di(4-methoxyphenyl)-9H-9-carbazoly]butyloxyl}piperazino)butyloxy]-(11aS)-1,2,3,11a-tetrahydro-5H-pyrrolo[2,1-c][1,4]benzodiazepin-5-one 18f, 7-methoxy-8-[3-(4-{3-[3,6-di(4-trifluoromethoxyphenyl)-9H-9-carbazoly]propyloxy}piperazino)propyloxy]-(11aS)-1,2,3,11a-tetrahydro-5H-pyrrolo[2,1-c][1,4]benzodiazepin-5-one 18g, 7-methoxy-8-[4-(4-{4-[3,6-di(4-trifluoromethoxyphenyl)-9H-9-carbazoly]butyloxy}piperazino)butyloxy]-(11aS)-1,2,3,11a-tetrahydro-5H-pyrrolo[2,1-c][1,4]benzodiazepin-5-one 18h, 7-methoxy-8-[5-(4-{5-[3,6-di(4-trifluoromethoxyphenyl)-9H-9-carbazoly]pentyloxy}piperazino)pentyloxy]-(11aS)-1,2,3,11a-tetrahydro-5H-pyrrolo[2,1-c][1,4]benzodiazepin-5-one 18i, 7-methoxy-8-[3-(4-{3-[3,6-di(4-fluorophenyl)-9H-9-carbazoly]propyloxy}piperazino)propyloxy]-(11aS)-1,2,3,11a-tetrahydro-5H-pyrrolo[2,1-c][1,4]benzodiazepin-5-one 18j, 7-methoxy-8-[4-(4-{-4-[3,6-di(4-fluorophenyl)-9H-9-carbazoly]butyloxy}piperazino)butyloxy]-(11aS)-1,2,3,11a-tetrahydro-5H-pyrrolo[2,1-c][1,4]benzodiazepin-5-one 18k, 7-methoxy-8-[5-(4-{5-[3,6-di(4-fluorophenyl)-9H-9-carbazoly]pentyloxy}piperazino)pentyloxy]-(11aS)-1,2,3,11a-tetrahydro-5H-pyrrolo[2,1-c][1,4]benzodiazepin-5-one 18l, 7-methoxy-8-[3-(4-{3-[3,6-di(4-chlorophenyl)-9H-9-carbazoly]propyloxy}piperazino)propyloxy]-(11aS)-1,2,3,11a-tetrahydro-5H-pyrrolo[2,1-c][1,4]benzodiazepin-5-one 18m, 7-methoxy-8-[4-(4-{4-[3,6-di(4-chlorophenyl)-9H-9-carbazoly]butyloxy}piperazino)butyloxy]-(11aS)-1,2,3,11a-tetrahydro-5H-pyrrolo[2,1-c][1,4]benzodiazepin-5-one 18n, 7-methoxy-8-[5-(4-{5-[3,6-di(4-chlorophenyl)-9H-9-carbazoly]pentyloxy}piperazino)pentyloxy]-(11aS)-1,2,3,11a-tetrahydro-5H-pyrrolo[2,1-c][1,4]benzodiazepin-5-one 18o, In another embodiment of present invention, carbazole linked pyrrolo[2,1-c][1,4]benzodiazepine hybrids of the structural formulae of the representative compounds are:

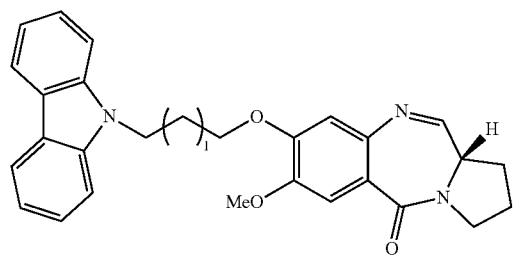
6a

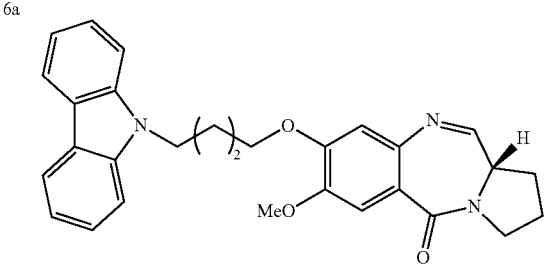
6b

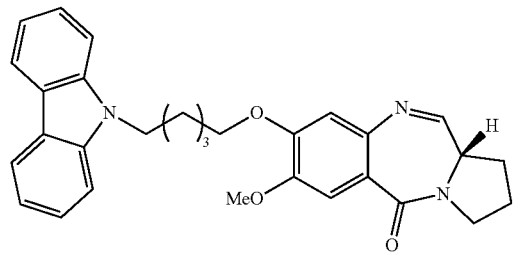
6c

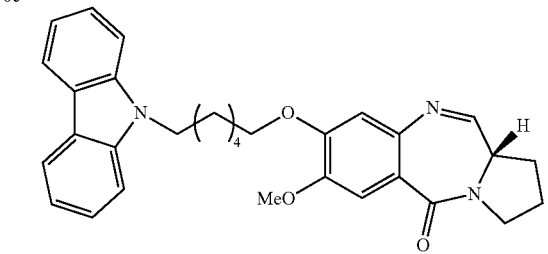
6d

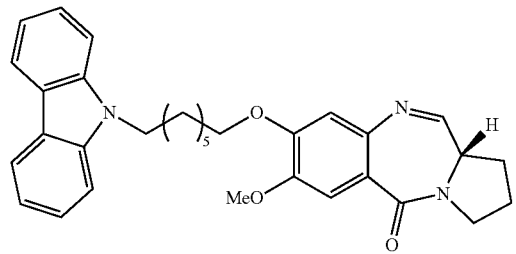
6e

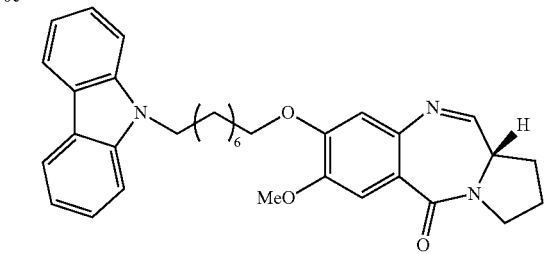
6f

-continued
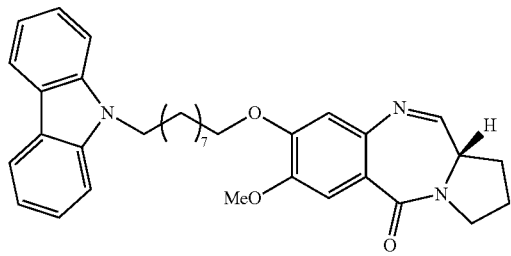
6g
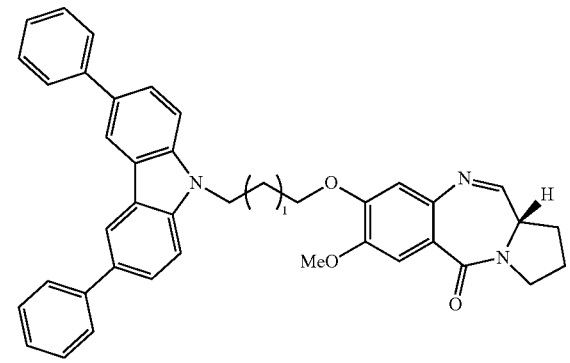
10a
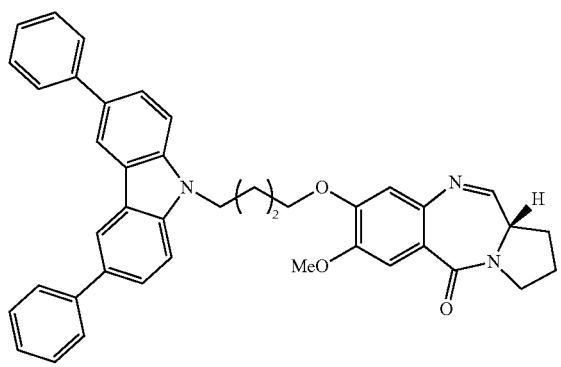
10b
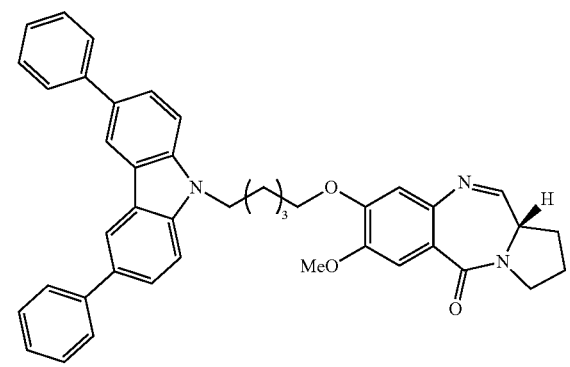
10c
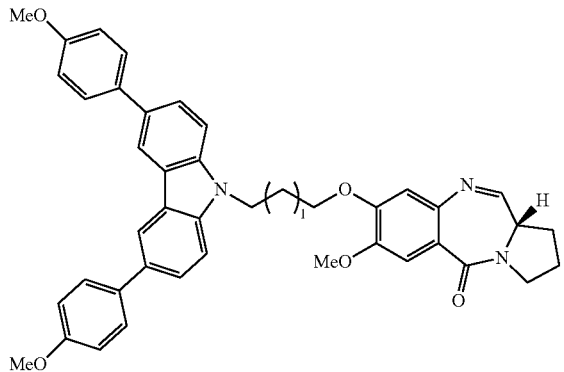
10d
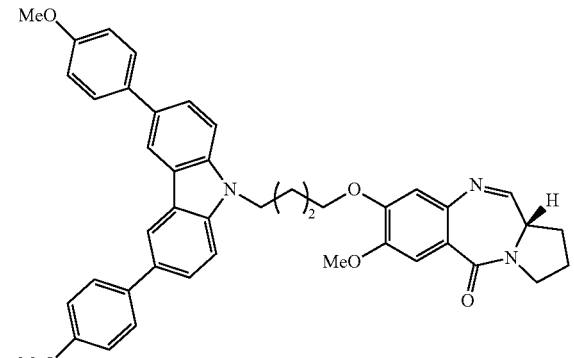
10e
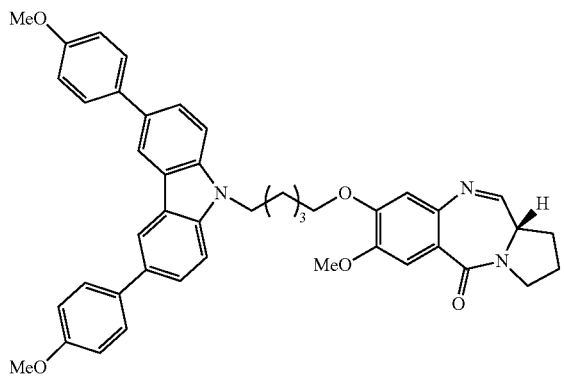
10f
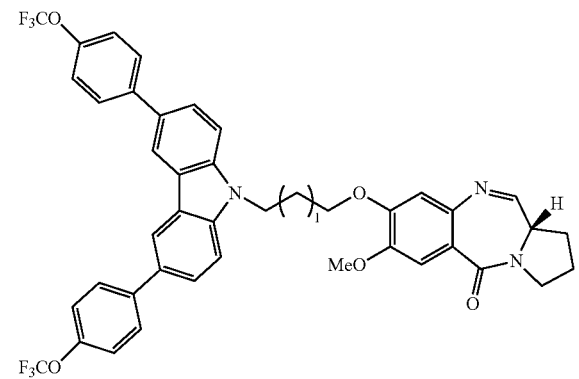
10g -continued
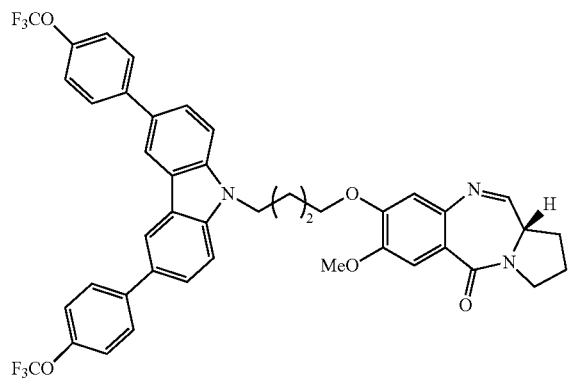
10h
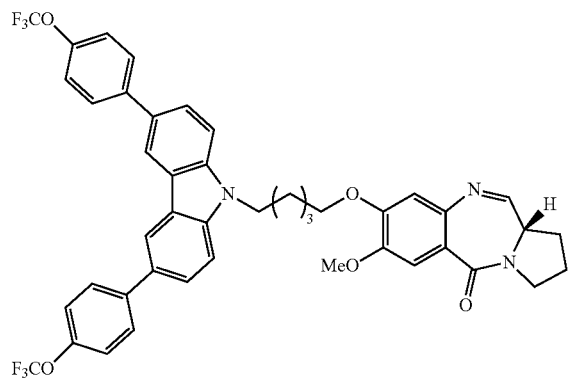
10i
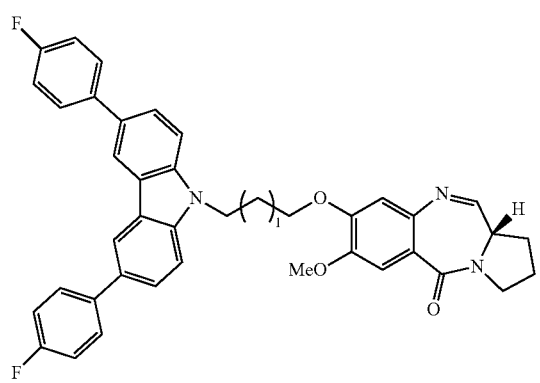
10j
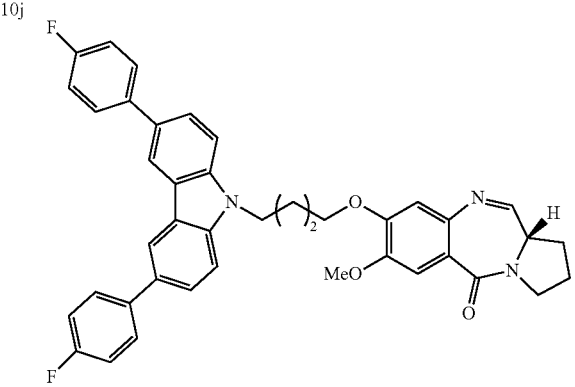
10k
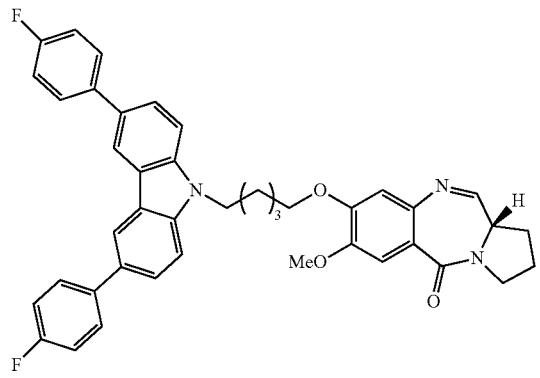
10l
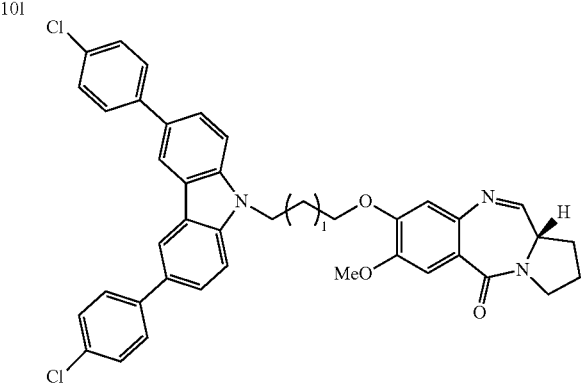
10m
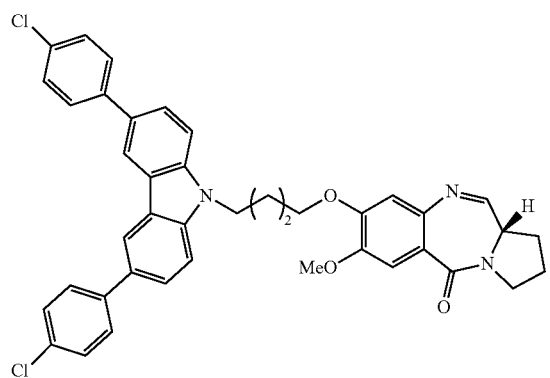
10n
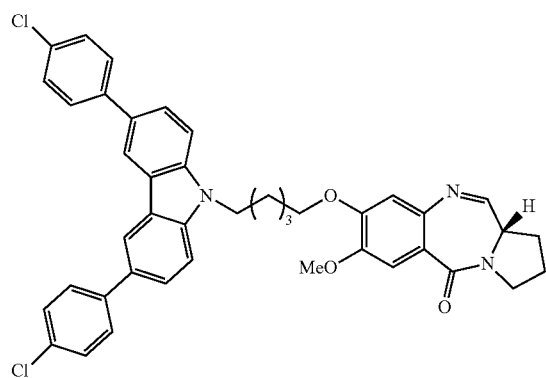
10o -continued
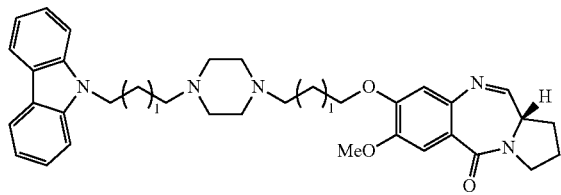
14a
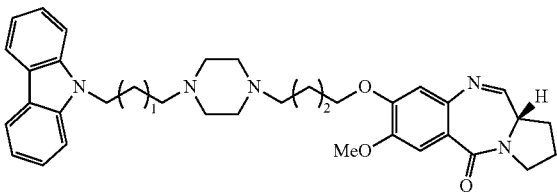
14b
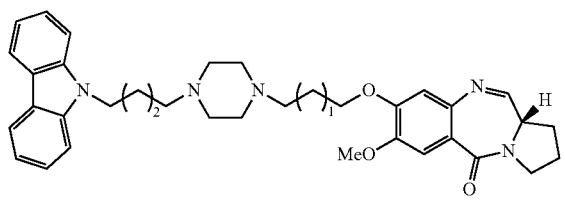
14c
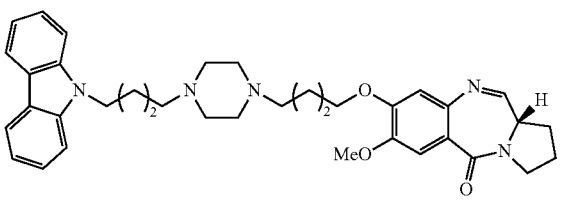
14d
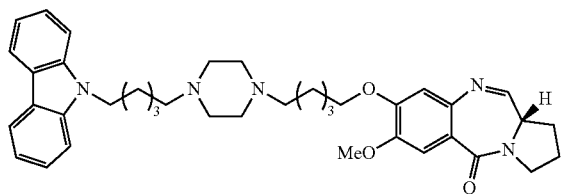
14e
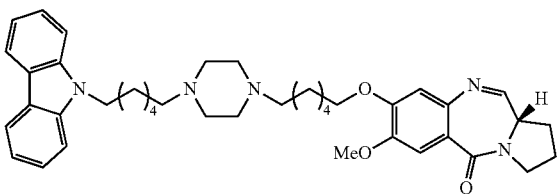
14f
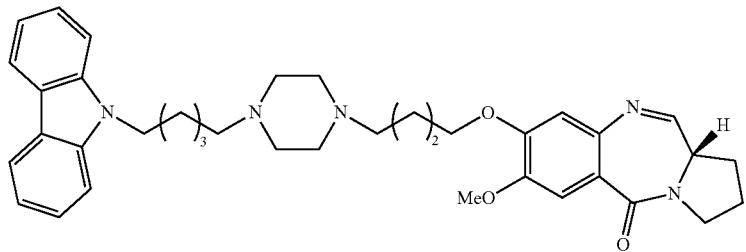
14g
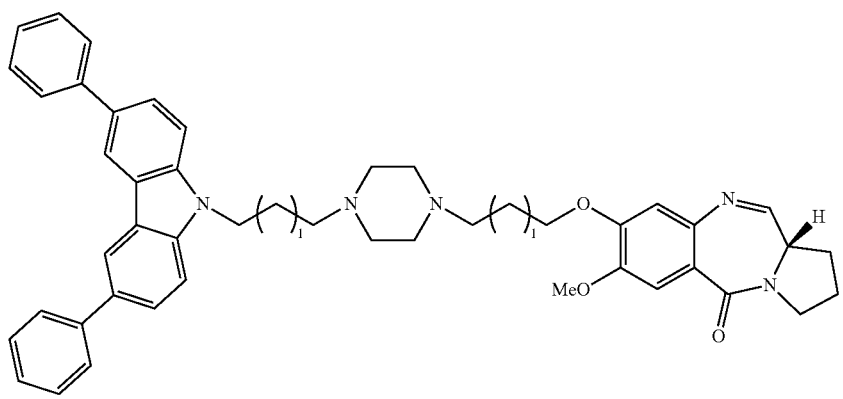
18a -continued
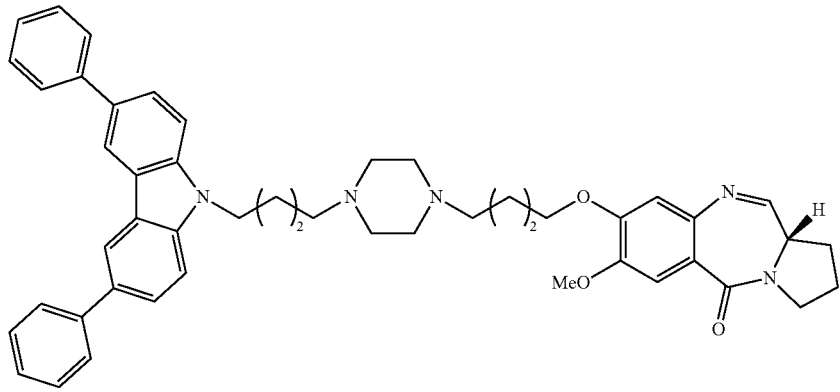
18b
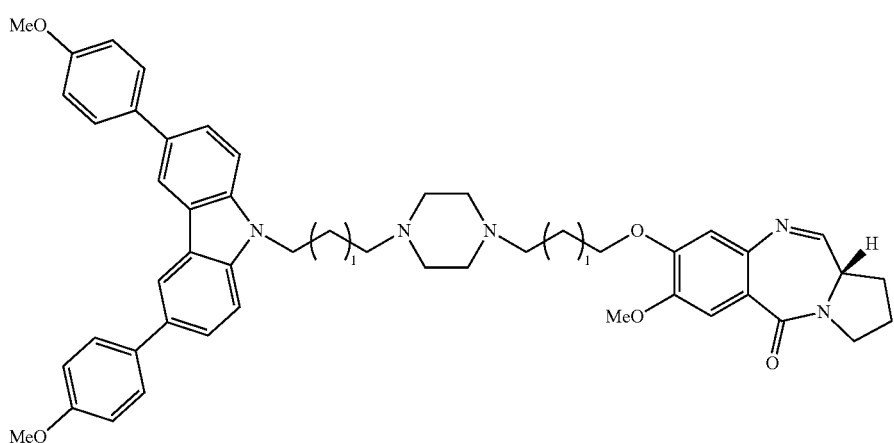
18c
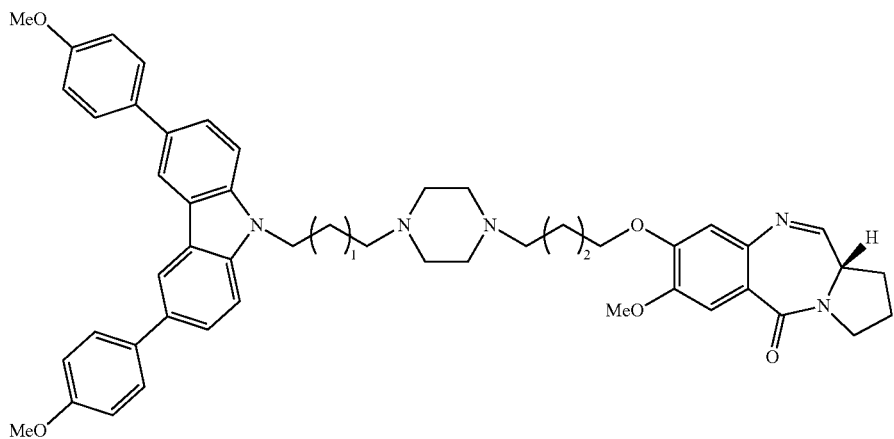
18d

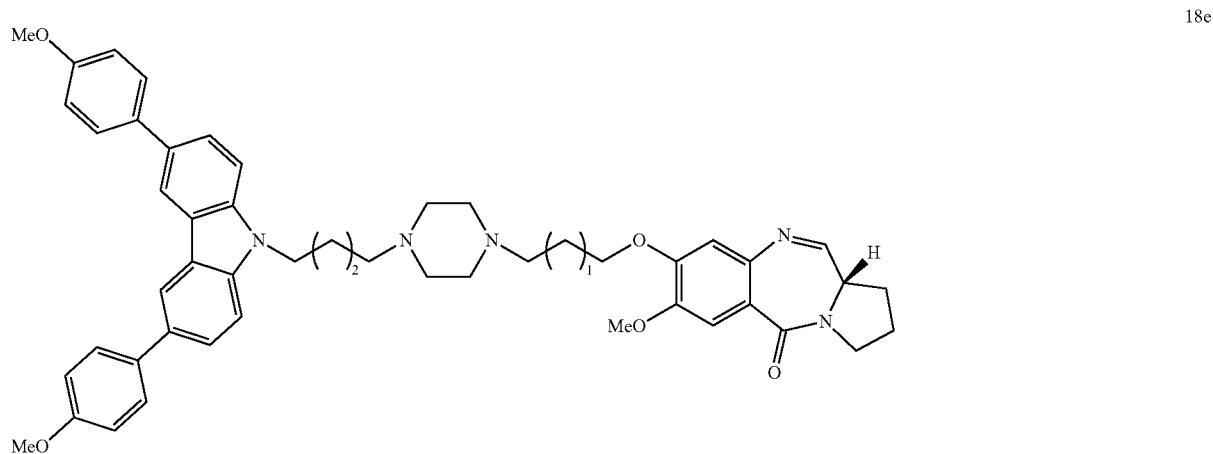
18e
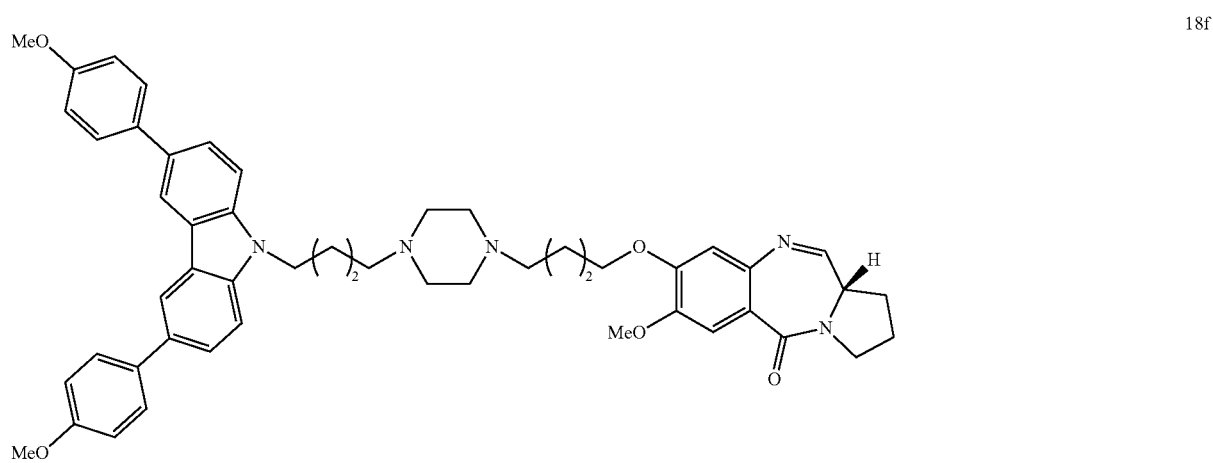
18f
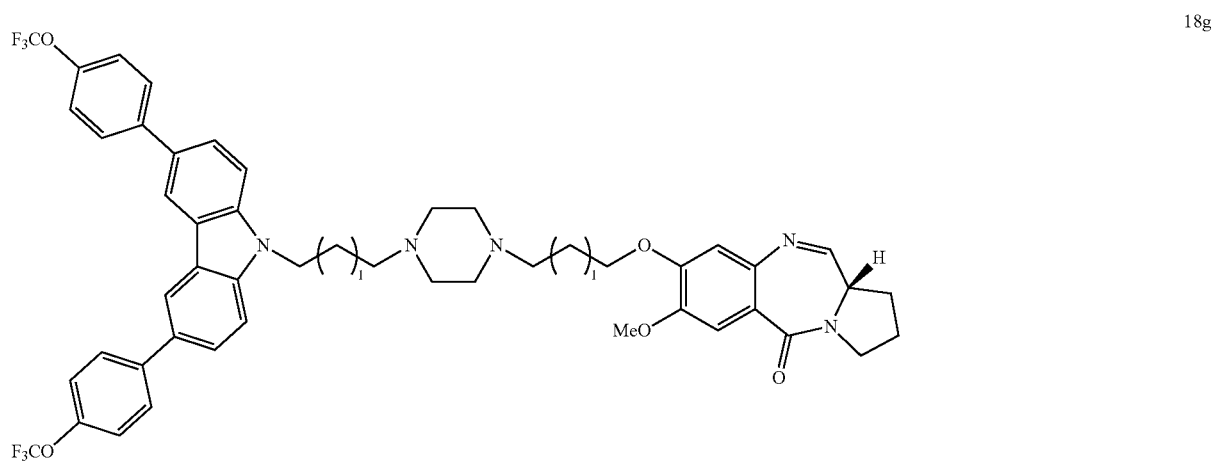
18g

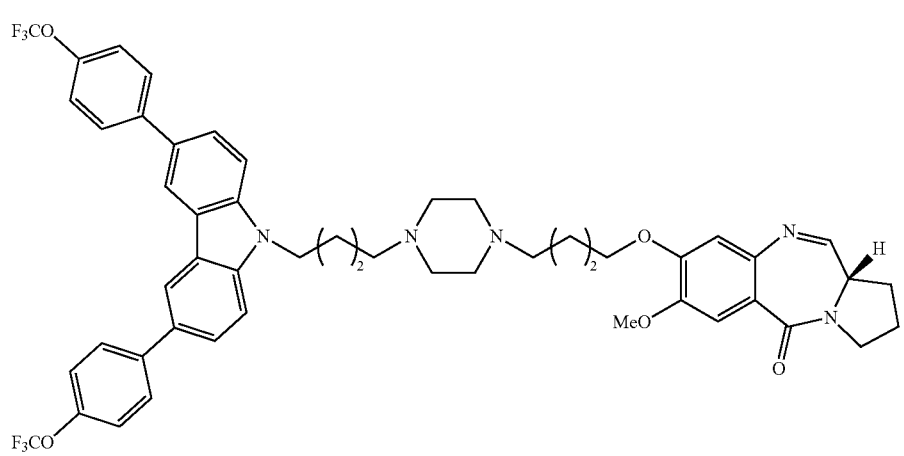
18h
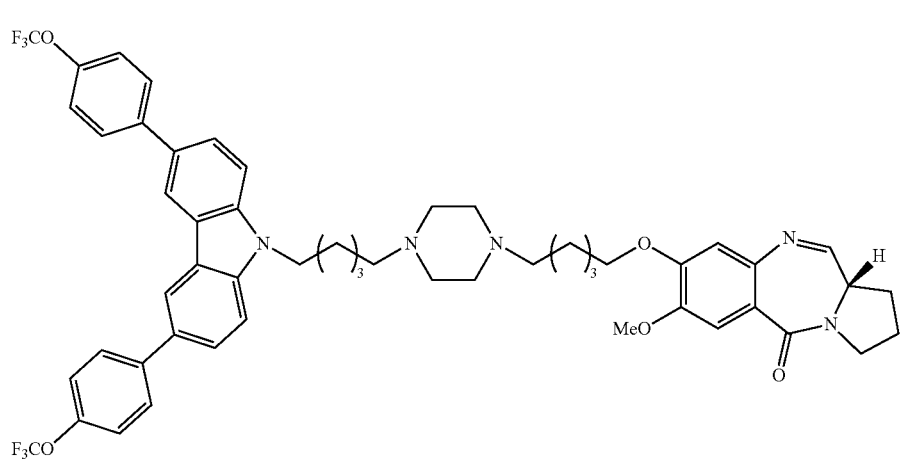
18i
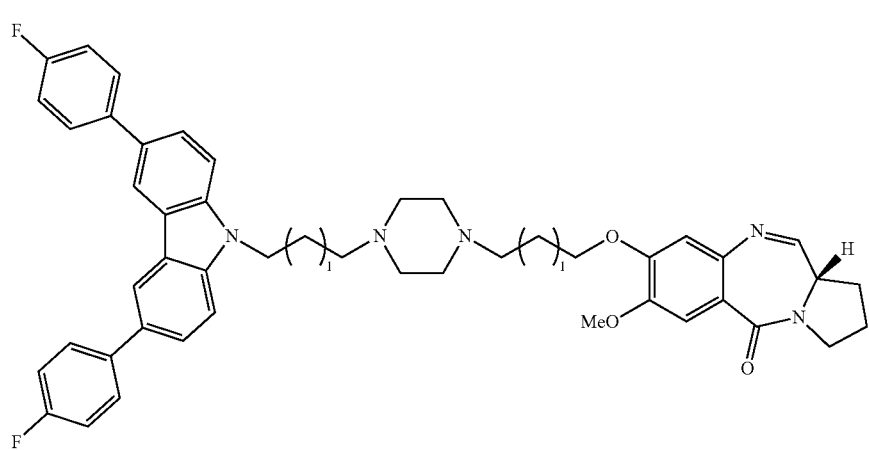
18j

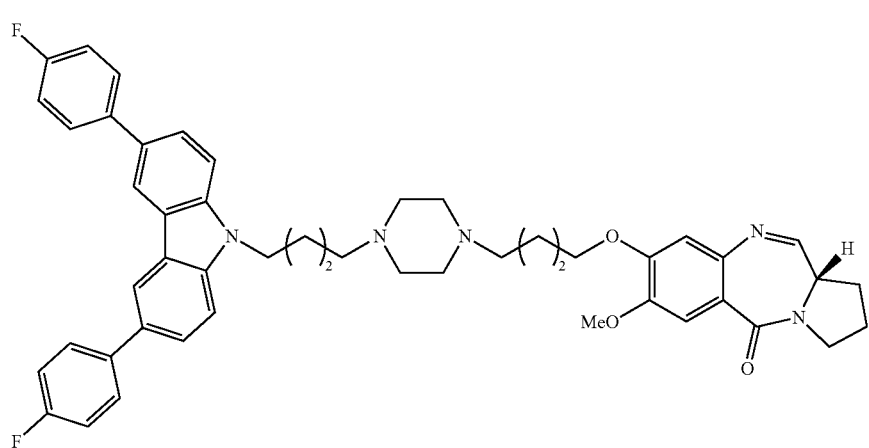
18k
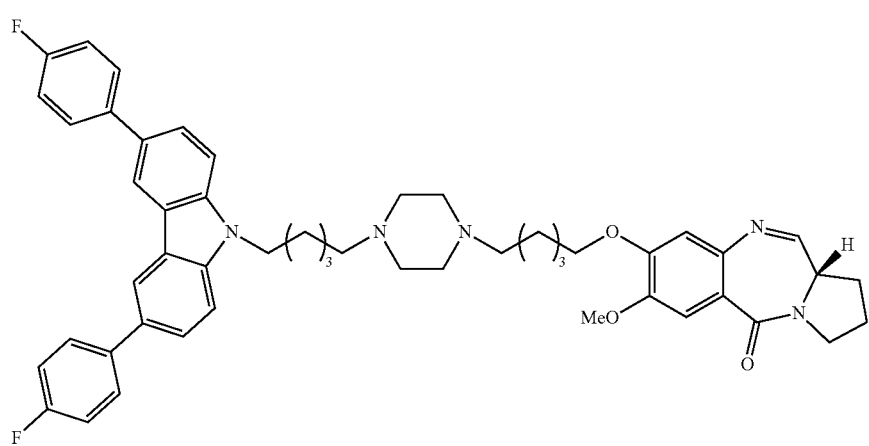
18l
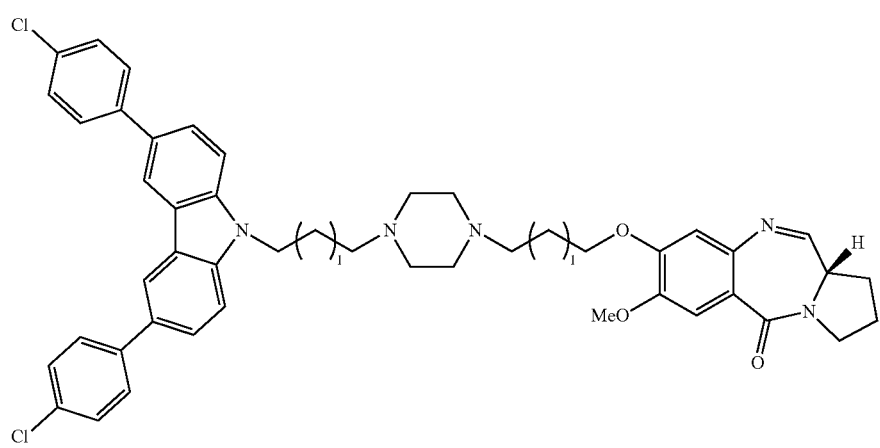
18m

-continued

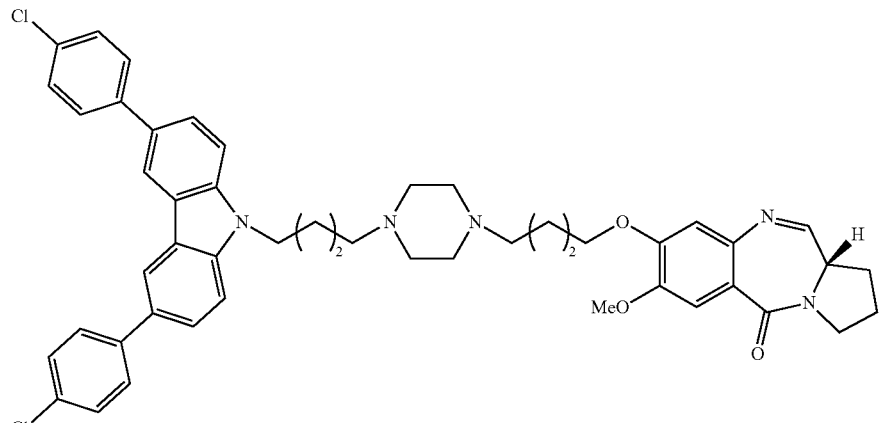

18n

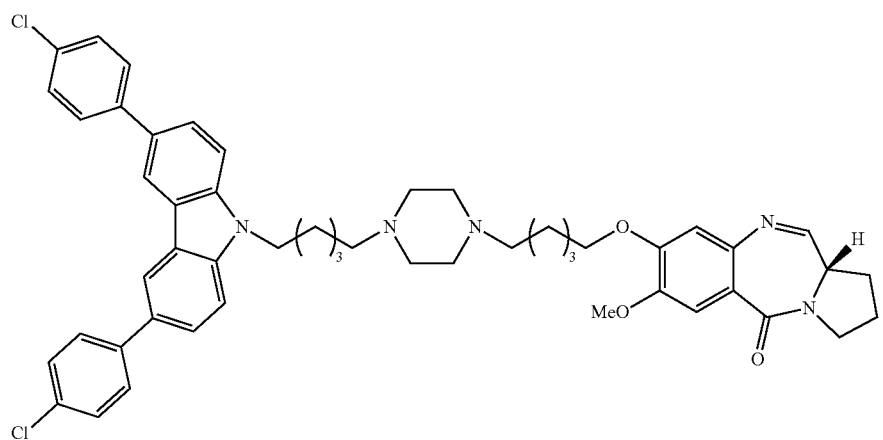

18o

In another embodiment of the present invention, carbazole linked pyrrolo[2,1-c][1,4]benzodiazepine 6c, exhibiting in vitro anticancer activity against human cancer cell lines selected from the group consisting of Leukemia Cancer cell lines (CCRF-CEM, MOLT-4, SR, HL-60(TB), K-562, RPMI-8226), CNS cancer cell lines (SF-268, SF-539, SNB-19, SNB-75, U251), Melanoma cancer cell lines (LOX IMVI, M14, SK-MEL-5, UACC-257, UACC-62, SK-MEL-28, MALME-3M, SK-MEL-2), Renal cancer cell lines (786-0, A498, ACHN, CAKI-1, RXF 393, SN12C, TK-10, UO-31), lung cancer cell lines (A549/ATCC, EKVX, HOP-62, HOP-92, NCI-H226, NCI-H23, NCI-H322M, NCI-H460, NCI-H522), breast cancer cell lines (MCF7, MDA-MB-, HS 578T, MDA-MB-435, BT-549, T-47D, MDA-MB-468), colon cancer cell lines (COLO 205, HCC-2998, HCT-116, HCT-15, HT29, KM12, SW-620), prostate cancer cell lines (DU145, PC3) and ovarian cancer cell lines (IGROV1, OVCAR-3, OVCAR-4, OVCAR-5, OVCAR-8, SK-OV-3).

In another embodiment of the present invention, carbazole linked pyrrolo[2,1-c][1,4]benzodiazepine 14a, exhibiting in vitro anticancer activity against human cancer cell lines selected from the group consisting of Leukemia Cancer cell lines (CCRF-CEM, MOLT-4, SR, HL-60(TB), CNS cancer cell lines (SF-268, SF-539, SNB-19, SNB-75, U251), Melanoma cancer cell lines (LOX IMVI, M14, SK-MEL-5, UACC-257, UACC-62, SK-MEL-28, MALME-3M, SK-MEL-2), Renal cancer cell lines (786-0, A498, ACHN, CAKI-1, RXF 393, SN12C, TK-10, UO-31), lung cancer cell lines (EKVX, HOP-62, HOP-92, NCI-H226, NCI-H23, NCI-H322M, NCI-H460, NCI-H522), breast cancer cell lines (MCF7, MDA-MB-, HS 578T, MDA-MB-435, BT-549, T-47D, MDA-MB-468), colon cancer cell lines (COLO 205, HCC-2998, HCT-116, HCT-15, HT29, KM12, SW-620), prostate cancer cell lines (DU145, PC3) and ovarian cancer cell lines (IGROV1, OVCAR-3, OVCAR-4, OVCAR-5, SK-OV-3).

In another embodiment of the present invention, carbazole linked pyrrolo[2,1-c][1,4]benzodiazepine 6c and 14a, wherein the concentration of the compound used for in vitro activity against leukemia cancer cell lines for $GI_{50}$ is in the range of 1.54 to 2.60, and 0.02 to 0.03 μm respectively at an exposure period of at least 48 hrs.

In another embodiment of the present invention, carbazole linked pyrrolo[2,1-c][1,4]benzodiazepine 6c and 14a, wherein the concentration of the compound used for in vitro activity against ovarian cancer cell lines for $GI_{50}$ is in the range of 1.88 to 4.57, and 0.01 to 0.29 μm respectively at an exposure period of at least 48 hrs.

In another embodiment of the present invention, carbazole linked pyrrolo[2,1-c][1,4]benzodiazepine 6c and 14a, wherein the concentration of the compound used for in vitro activity against lung cancer cell lines for $GI_{50}$ is in the range of 1.31 to 5.27, and 0.01 to 0.27 μm respectively at an exposure period of at least 48 hrs.

In another embodiment of the present invention, carbazole linked pyrrolo[2,1-c][1,4]benzodiazepine 6c and 14a, wherein the concentration of the compound used for in vitro activity against renal cancer cell lines for $GI_{50}$ is in the range of 1.52 to 4.34, and 0.12 to 0.27 μm respectively at an exposure period of at least 48 hrs.

In another embodiment of the present invention, carbazole linked pyrrolo[2,1-c][1,4]benzodiazepine 6c and 14a, wherein the concentration of the compound used for in vitro activity against Colon cancer cell lines for $GI_{50}$ is in the range of 1.65 to 2.11, and 0.04 to 0.28 μm respectively at an exposure period of at least 48 hrs.

In another embodiment of the present invention, carbazole linked pyrrolo[2,1-c][1,4]benzodiazepine 6c and 14a, wherein the concentration of the compound used for in vitro activity against Breast cancer cell lines for $GI_{50}$ is in the range of 1.73 to 2.79, and 0.01 to 0.95 μM respectively at an exposure period of at least 48 hrs.

In another embodiment of the present invention, carbazole linked pyrrolo[2,1-c][1,4]benzodiazepine 6c and 14a, wherein the concentration of the compound used for in vitro activity against CNS cancer cell lines for $GI_{50}$ is in the range of 1.05 to 2.05, and 0.03 to 0.21 μm respectively at an exposure period of at least 48 hrs.

In another embodiment of the present invention, carbazole linked pyrrolo[2,1-c][1,4]benzodiazepine 6c and 14a, wherein the concentration of the compound used for in vitro activity against Prostate cell lines for $GI_{50}$ is in the range of 2.23 to 2.36, and 0.03 to 0.04 μm respectively at an exposure period of at least 48 hrs.

In another embodiment of the present invention, carbazole linked pyrrolo[2,1-c][1,4]benzodiazepine 6c and 14a, wherein the concentration of the compound used for in vitro activity against Melanoma cancer cell lines for $GI_{50}$ is in the range of 1.67 to 2.29, and 0.03 to 0.23 nm respectively at an exposure period of at least 48 hrs.

In another embodiment of the present invention, carbazole linked pyrrolo[2,1-c][1,4]benzodiazepine, wherein the compound 6c exhibits in-vitro cytotoxicity in mean graph midpoint value of −5.67 (mol/lit), −5.29 (mol/lit), and −4.67 (mol/lit) for $\log_{10} GI_{50}$, $\log_{10} TGI$ and $\log_{10}a LC_{50}$, respectively, against nine human tumor cell lines.

In another embodiment of the present invention, carbazole linked pyrrolo[2,1-c][1,4]benzodiazepine, wherein the compound 14a exhibits in-vitro cytotoxicity data in mean graph midpoint value of −6.96, −6.24, and −5.57 for $\log_{10} GI_{50}$, $\log_{10} TGI$ and $\log_{10} LC_{50}$, respectively, against nine human tumor cell lines.

In another embodiment of the present invention, carbazole linked pyrrolo[2,1-c][1,4]benzodiazepine, wherein the compound 6a exhibits in-vitro cytotoxicity in breast (MCF-7) $GI_{50}$ (1.85 μmol/L), colon (Colo205) $GI_{50}$ (1.68 μmol/L) and non small cell lung (HOPO62) $GI_{50}$ (1.93 μmol/L) cancer cell lines respectively.

In another embodiment of the present invention, carbazole linked pyrrolo[2,1-c][1,4]benzodiazepine, wherein the compound 6b exhibits in-vitro cytotoxicity in breast (Zr-75-1) $GI_{50}$ (1.81 μmol/L), colon (Colo 205) $GI_{50}$ (1.70 μmol/L) and non small cell lung (HOPO 62) $GI_{50}$ (1.93 μmol/L) cancer cell lines respectively.

In another embodiment of the present invention, carbazole linked pyrrolo[2,1-c][1,4]benzodiazepine, wherein the compound 6d exhibits in-vitro cytotoxicity in breast (MCF-7) $GI_{50}$ (1.65 μmol/L), colon (Colo205) $GI_{50}$ (1.62 μmol/L) and non small cell lung (HOPO62) $GI_{50}$ (1.58 μmol/L) cancer cell lines respectively.

In another embodiment of the present invention, carbazole linked pyrrolo[2,1-c][1,4]benzodiazepine, wherein the compound 14b exhibits in-vitro cytotoxicity in breast (MCF-7) and (Zr-75-1) $GI_{50}$(0.15 and 0.15 μmol/L), colon (Colo205) $GI_{50}$ (0.14 μmol/L) and non small cell lung (HOPO62) $GI_{50}$ (0.14 μmol/L) cancer cell lines respectively.

In another embodiment of the present invention, carbazole linked pyrrolo[2,1-c][1,4]benzodiazepine, wherein the compound 14d exhibits in-vitro cytotoxicity in breast (MCF-7) and (Zr-75-1) $GI_{50}$ (0.15 and 0.17 μmol/L), colon (Colo205) $GI_{50}$ (0.16 μmol/L) and oral (KB and GURAV) $GI_{50}$ (0.15 and 0.17 μmol/L) cancer cell lines respectively.

In another embodiment of the present invention, carbazole linked pyrrolo[2,1-c][1,4]benzodiazepine, wherein the compound 10d exhibits in-vitro cytotoxicity in breast (MCF-7) $GI_{50}$ (0.13 μmol/L), colon (Colo205) $GI_{50}$ (1.70 μmol/L) and non small cell lung (HOPO62) $GI_{50}$ (0.11 μmol/L) cancer cell lines respectively.

In another embodiment of the present invention, carbazole linked pyrrolo[2,1-c][1,4]benzodiazepine, wherein the compound 10e exhibits in-vitro cytotoxicity in prostate (PC-3) $GI_{50}$ (0.16 μmol/L), Cervix (Si-Ha) $GI_{50}$ (0.17 μmol/L) and Breast (MCF-7) $GI_{50}$ (0.15 μmol/L) cancer cell lines respectively.

In another embodiment of the present invention, A process for the preparation of carbazole linked pyrrolo[2,1-c][1,4] benzodiazepine hybrids of formulae A.

Formula A

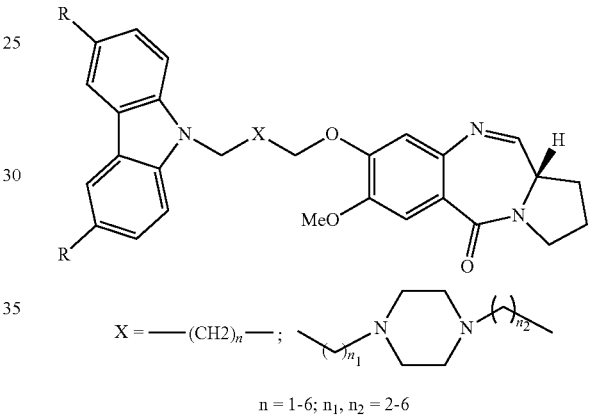

$n = 1\text{-}6; n_1, n_2 = 2\text{-}6$

R = H, Ph, 4-OMe(Ph), 4-OCF$_3$(Ph), 4-F, 4-Cl a) adding substituted [5-methoxy-2-nitrobenzoyl)]pyrrolidine-2-carboxaldehydediethylthioacetal of formula 1 and 2 with carbazole of formulae 3, 7, 11 and 15 in mole ratio ranging between 1-1.5 in an organic solvent in the presence of inorganic base, 1a-g

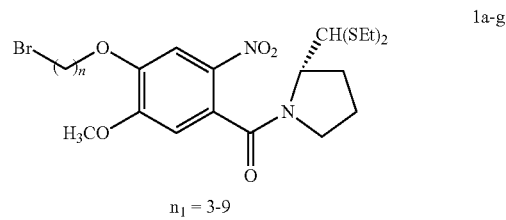

$n_1 = 3\text{-}9$ 2a-d

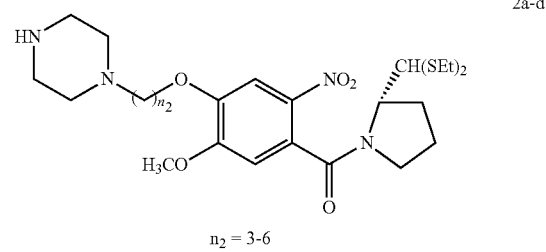

$n_2 = 3\text{-}6$

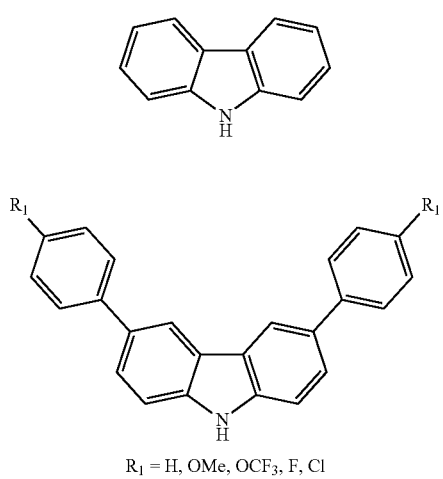

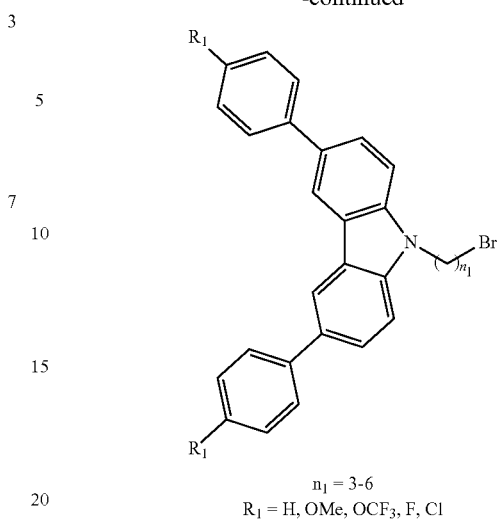

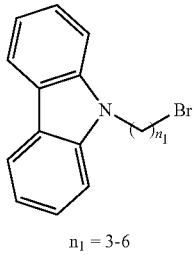

b) refluxing reaction mixture as obtained in step (a) at temperature ranging between 70-80° C. for a period of ranging between 24-48 h;
c) removing the inorganic base from the reaction mixture as obtained in step (b) by filtration and evaporating the organic solvent to obtain the resultant crude product;
d) purifying the crude product as obtained in step (c) by column chromatography using ethyl acetate-hexane (1:1) as a solvent system to obtain the desired product of formulae 4a-g, 8a-o, 12a-g and 16a-o.

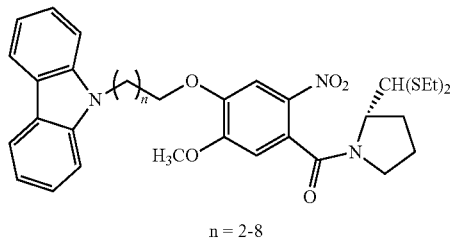

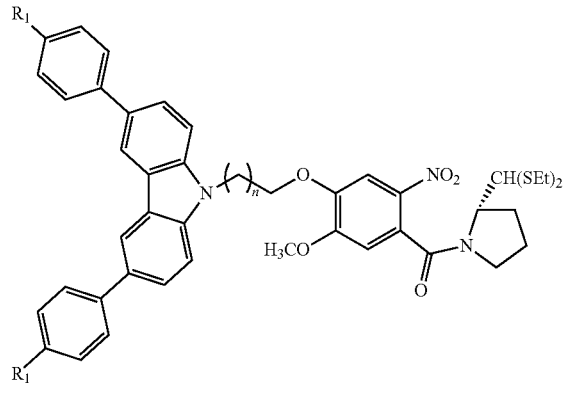

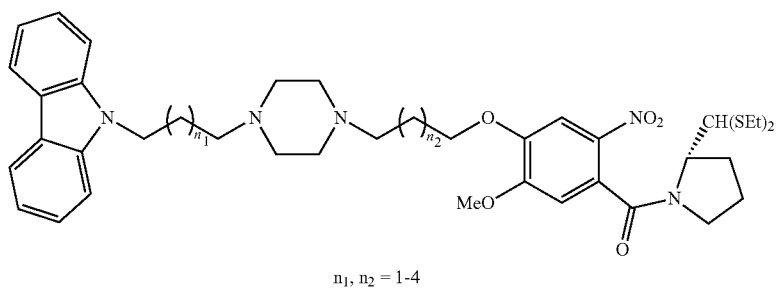

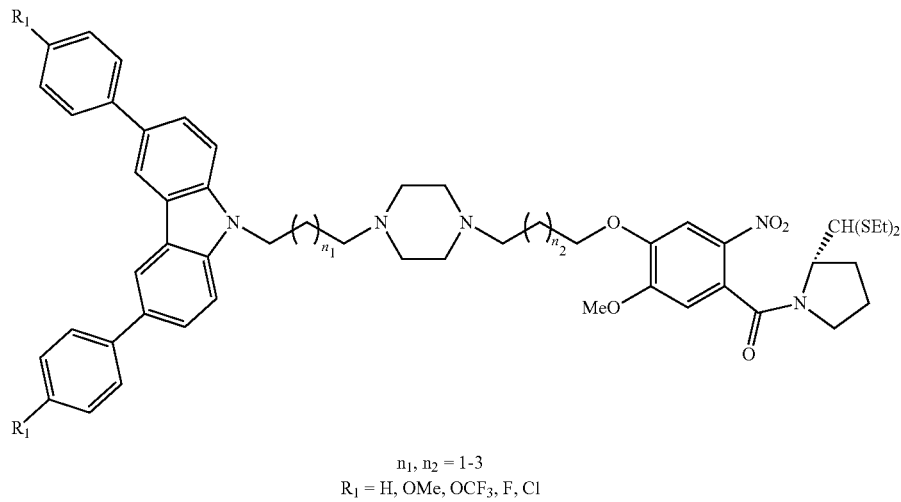

Formula-16a-o $n_1, n_2 = 1-3$
$R_1 = H, OMe, OCF_3, F, Cl$ e) refluxing the compounds of formulae 4a-g, 8a-o, 12a-g and 16a-o as obtained in step (d) with SnCl$_2$,2H$_2$O in an alcohol to reduce;

f) evaporating the alcohol from reaction mixture as obtained in step (e) and adjusting the pH of the resultant product layer in the range of 7-8 by using a base followed by extraction with ethyl acetate and washing the combined organic phase with brine solution.

g) evaporating the solvent from washed organic phase to obtain the desired products of formulae 5a-g, 9a-o, 13a-g and 17a-o.

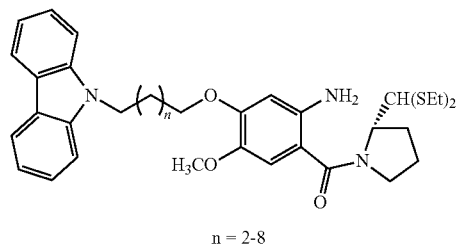

5a-g n = 2-8

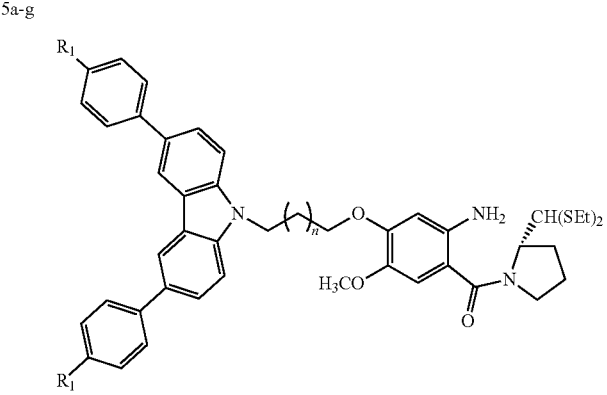

9a-o n = 2-8
$R_1 = H, OMe, OCF_3, F, Cl$

Formula-13a-g

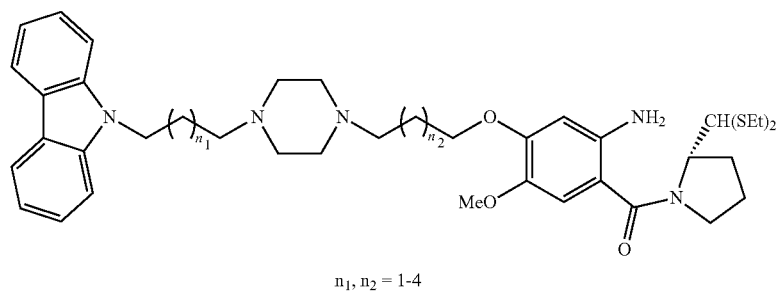

$n_1, n_2 = 1-4$

-continued

Formula-17a-o

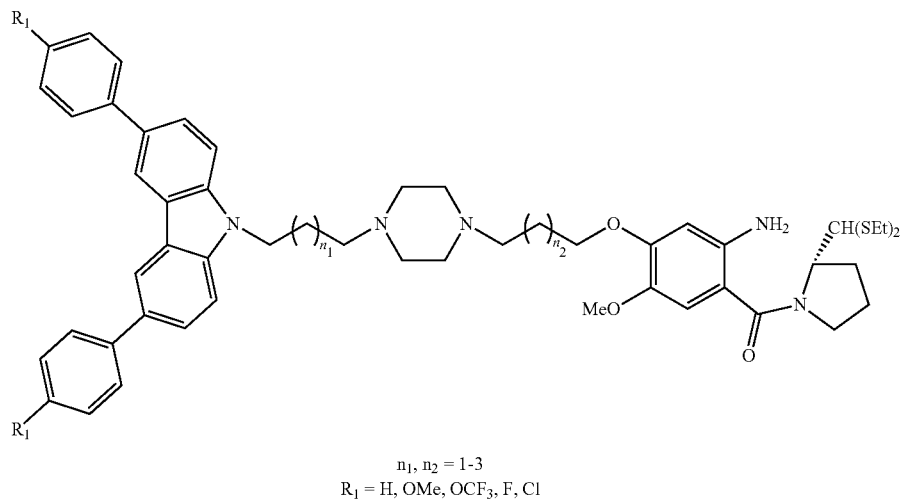

n₁, n₂ = 1-3
R₁ = H, OMe, OCF₃, F, Cl h) stirring the compound of formulae 5a-g, 9a-o, 13a-g and 17a-o as obtained in step (g) with HgCl₂ and CaCO₃ in a solvent preferably acetonitrile:water (4:1) at temperature ranging between 24-27° C. for a period ranging between 12-16 h.

i) extracting the clear organic supernatant from reaction mixture as obtained in step (h) with ethyl acetate and washed with saturated 5% NaHCO₃ and brine followed by drying the organic layer over Na₂SO₄ to obtain anhydrous organic layer j) evaporating organic solvent from organic layer as obtained in step (i) to obtain white solid.

k) purifying the white solid as obtained in step (j) by column chromatography using ethyl acetate as a solvent system to obtain compounds of formulae 6a-g, 10a-o, 14a-g and 18a-o.

In another embodiment of the present invention, a process as claimed in step (a), wherein substituted [5-methoxy-2-nitrobenzoyl)]pyrrolidine-2-carboxaldehydediethylthioacetal is selected from the group of (2S)—N-[(n-bromoalkyloxy)-3-methoxy-2-nitrobenzoyl)]pyrrolidine-2-carboxaldehydediethylthioacetal and (2S)-[N-{n-(3-(piperzin-1-yl)alkyl}-5-methoxy-2-nitrobenzoyl]pyrrolidine-2-carboxaldehyde diethylthioacetal.

In another embodiment of the present invention, a process as claimed in step (a), wherein organic solvent used is acetone.

In another embodiment of the present invention, a process as claimed in step (a), wherein inorganic base used is potassium carbonate.

In another embodiment of the present invention, a process as claimed in step (e), wherein alcohol used is methanol.

In another embodiment of the present invention, a process as claimed in step (f), wherein base used to adjust pH is 10% NaHCO₃.

DETAILED DESCRIPTION OF THE INVENTION

The precursors carbazole of formulae 7 and 15 have been prepared literature method (U. Jacquemard, S. Routier, A. Tatibouef, J. Wluzu, W. Laine, C. Bal, C. billy and J. Merour (*Org. Biomol. Chem.*, 2004, 2, 1476-1483).

1H-1-pyrrolyl(4-hydroxy-5-methoxy-2-nitrophenyl) methanone of formula 1 (Thurston, D. E.; Murthy, V. S.; Langley, D. R.; Jones, G. B, *Synthesis.* 1990, 81) has been prepared by literature method.

Some representative compounds of formulae 6a-g, 10a-o, 14a-g and 18a-o for the present inventions are given below
7-methoxy-8-[3-(9H-9-carbazoly)propyloxy]-(11aS)-1,2,3,11a-tetrahydro-5H-pyrrolo[2,1-c][1,4]benzodiazepin-5-one 6a,
7-methoxy-8-[4-(9H-9-carbazoly)butyloxy]-(11aS)-1,2,3,11a-tetrahydro-5H-pyrrolo[2,1-c][1,4]benzodiazepin-5-one 6b,
7-methoxy-8-[5-(9H-9-carbazoly)pentyloxy]-(11aS)-1,2,3,11a-tetrahydro-5H-pyrrolo[2,1-c][1,4]benzodiazepin-5-one 6c,
7-methoxy-8-[6-(9H-9-carbazoly)hexyloxy]-(11aS)-1,2,3,11a-tetrahydro-5H-pyrrolo[2,1-c][1,4]benzodiazepin-5-one 6d,
7-methoxy-8-{3-[3,6-di(4-methoxyphenyl)-9H-9-carbazoly]propyloxy}-(11aS)-1,2,3,11a-tetrahydro-5H-pyrrolo[2,1-c][1,4]benzodiazepin-5-one 10d,
7-methoxy-8-{4-[3,6-di(4-methoxyphenyl)-9H-9-carbazoly]butyloxy}-(11aS)-1,2,3,11a-tetrahydro-5H-pyrrolo[2,1-c][1,4]benzodiazepin-5-one 10e,
7-methoxy-8-(3-{4-[3-(9H-9-carbazoly)propyloxy]piperazino}propyloxy)-(11aS)-1,2,3,11a-tetrahydro-5H-pyrrolo[2,1-c][1,4]benzodiazepin-5-one 14a,
7-methoxy-8-(3-{4-[4-(9H-9-carbazoly)butyloxy]piperazino}propyloxy)-(11aS)-1,2,3,11a-tetrahydro-5H-pyrrolo[2,1-c][1,4]benzodiazepin-5-one 14b,
7-methoxy-8-(4-{4-[3-(9H-9-carbazoly)propyloxy]piperazino}butyloxy)-(11aS)-1,2,3,11a-tetrahydro-5H-pyrrolo[2,1-c][1,4]benzodiazepin-5-one 14c,
7-methoxy-8-(4-{4-[4-(9H-9-carbazoly)butyloxy]piperazino}butyloxy)-(11aS)-1,2,3,11a-tetrahydro-5H-pyrrolo[2,1-c][1,4]benzodiazepin-5-one 14d,
7-methoxy-8-[3-(4-{3-[3,6-di(4-methoxyphenyl)-9H-9-carbazoly]propyloxy}piperazino) proyloxy]-(11aS)-1,2,3,11a-tetrahydro-5H-pyrrolo[2,1-c][1,4]benzodiazepin-5-one 18c, These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This resulted in design and synthesis of new congeners as illustrated in Scheme-1, Scheme-2, Scheme-3, and Scheme-4 which comprise:
1. The ether linkage at C-8 position of DC-81 intermediates with the compounds of formulae 2, 6 and 14.
2. Refluxing the reaction mixtures for 48 h.
3. Synthesis of C-8 linked PBD antitumour antibiotic hybrid imines.
4. Purification by column chromatography using different solvents like ethylacetate, hexane, dichloromethane and methanol.

The following examples are given by way of illustration and therefore should not be construed to the present limit of the scope of invention.

EXAMPLE-1

7-Methoxy-8-[3-(9H-9-carbazoly)propoxy]-(11aS)-1,2,3,11a-tetrahydro-5H-pyrrolo[2,1-c][1,4]-benzo-diazepin-5-one 6a To a solution of 2S—N-[4-(3-bromopropoxy)-5-methoxy-2-nitrobenzoyl]pyrrolidine-2-carboxaldehyde diethylthioacetal (1a) (521 mg, 1.0 mmol) in dry acetone (20 mL) was added anhydrous potassium carbonate (690 mg, 5.0 mmol) and carbazole (3) (252 mg, 1.0 mmol). The reaction mixture was refluxed in an oil bath for 24 h at 80° C. and the reaction was monitored by TLC using ethyl acetate-hexane (1:1) as a solvent system. The potassium carbonate was then removed by suction filtration and the solvent was evaporated under vacuum to afford the crude product. This was further purified by column chromatography using ethyl acetate:hexane (6:4) as a solvent system to obtain the pure product (4a) (486 mg, 80% yield).

$^1$H NMR (CDCl$_3$): δ 8.02 (d, 2H, J=7.554 Hz), 7.55 (s, 1H), 7.40 (t, 2H, J=8.309 Hz), 7.35 (t, 2H, J=7.74 Hz), 6.86 (s, 1H), 4.87 (d, 1H, J=3.77, Hz), 4.68 (m, 1H), 4.61 (t, 2H), 4.05 (s, 3H), 3.91-4.0 (m), 3.18-3.2 (m), 2.69-2.87 (m), 2.45 (t, 2H), 2.25 (m, 2H), 2.12 (m, 1H), 1.97 (m), 1.82 (m), 1.39 (m, 9H).

FABMS: 608 (M+H)$^+$.

To a compound of 4a (692.85 mg, 1.0 mmol) in methanol (10 mL), SnCl$_2$.2H$_2$O (1.12 g, 5.0 mmol) was added and refluxed until the TLC indicated the completion of the reaction. The methanol was then evaporated in vacuum and the aqueous layer was then adjusted to pH 8 with 10% NaHCO$_3$ solution and extracted with ethyl acetate (60 mL). The combined organic phase was dried over Na$_2$SO$_4$ and evaporated under vacuum to afford the crude amino diethylthioacetal 5a (638 mg, 97% yield), which was directly used in the next step.

A solution of 5a (662.26 mg, 1.0 mmol), HgCl$_2$ (576 mg, 2.26 mmol) and CaCO$_3$ (225 mg, 2.46 mmol) in acetonitrile-water (4:1) was stirred slowly at room temperature (27° C.) overnight (12 h) until complete consumption of starting material as indicated by the TLC. The clear organic supernatant liquid was extracted with ethyl acetate and washed with saturated 5% NaHCO$_3$ (20 mL), brine (20 mL) and the combined organic phase was dried over Na$_2$SO$_4$. The organic layer was evaporated in vacuum to afford a white solid, which was first eluted on a column chromatography with ethyl acetate to remove mercuric salts, and then with ethyl acetate to obtain the pure product 6a (265 mg, 58% yield).

$^1$H NMR (CDCl$_3$): δ 8.05 (d, 2H), 7.61 (d, 1H J=4.52 Hz), 7.55 (s, 1H), 7.45 (d, 2H, J=8.30 Hz), 7.35 (m, 2H), 7.18 (m, 2H, J=7.74 Hz), 6.65 (s, 1H), 4.62 (m, 1H), 4.20-4.41 (m), 4.05 (s, 3H), 3.91-4.0 (m), 3.52-3.73 (m), 2.46 (m, 4H), 2.31 (m), 2.05 (m), 1.67 (m), 1.37 (m).

FABMS: 454 (M+H)$^+$.

EXAMPLE-2

7-Methoxy-8-[4-(9H-9-carbazoly)butoxy]-(11aS)-1,2,3,11a-tetrahydro-5H-pyrrolo[2,1-c][1,4]benzodiazepin-5-one 6b This compound was prepared according to the method described for the compound 4a by employing 2S—N-[4-(4-bromobutoxy)-5-methoxy-2-nitrobenzoyl]pyrrolidine-2-carboxaldehyde diethylthioacetal (1b) (535 mg, 1.0 mmol) was added anhydrous potassium carbonate (690 mg, 5.0 mmol) and carbazole (3) to obtain the pure product (252 mg, 1.0 mmol). 4b (522 mg, 84% yield).

$^1$H NMR (CDCl$_3$): δ, 8.04 (d 2H, J=7.55 Hz), 7.55 (s, 1H), 7.4 (m), 7.18 (m, 2H, J=7.74), 6.78 (s, 1H), 4.82 (d, 2H J=3.77 Hz), 4.65 (m, 1H), 4.45 (t, 2H), 4.05 (m, 2H), 3.92 (s, 3H), 3.72 (t, 2H), 3.22 (m), 2.65-2.82 (m), 1.92 (m, 2H), 1.82 (m), 1.39 (m, 6H).

FABMS: 622 (M+H)$^+$.

This compound was prepared according to the method described for the compound 5a by reducing 4b (706 mg, 1.0 mmol) using SnCl$_2$.2H$_2$O (1.12 g, 5.0 mmol). The amino compound 5b obtained was (651 mg, 97% yield).

This compound was prepared according to the method described for the compound 6a employing 5b (676.89 mg, 1.0 mmol) and HgCl$_2$ (582 mg, 2.26 mmol), CaCO$_3$ (230 mg, 2.46 mmol) in acetonitrile-water (4:1) to obtain the pure product 6b (309 mg, 58% yield).

$^1$H NMR (CDCl$_3$): δ 8.05 (d, 2H J=7.324 Hz), 7.60 (d, 1H, J=3.66 Hz), 7.32-7.42 (m, 4H, J=8.05 Hz), 4.35 (t, 2H, J=6.5 Hz), 3.92-4.2 (m), 3.90 (s, 3H), 3.42-3.74 (m), 2.29 (t, 2H), 1.74-2.12 (m), 1.6 (m), 1.42 (m, J=7.32 Hz).

FABMS: 468 (M+H)$^+$.

EXAMPLE-3

7-Methoxy-8-[5-(9H-9-carbazoly)pentyloxy]-(11aS)-1,2,3,11a-tetrahydro-5H-Pyrrolo[2,1-c][1,4]benzodiazepin-5-one 6c This compound was prepared according to the method described for the compound 4a by employing 2S—N-[4-(5-bromopentyloxy)-5-methoxy-2-nitrobenzoyl]pyrrolidine-2 carboxaldehyde diethylthioacetal (1c) (549 mg, 1.0 mmol) was added anhydrous potassium carbonate (690 mg, 5.0 mmol) and carbazole (3) (252 mg, 1.0 mmol) to obtain the pure product 4c (553 mg, 87% yield).

$^1$H NMR (CDCl$_3$): δ 8.04 (d, 2H, J=7.55 Hz), 7.55 (s, 1H), 7.4 (m), 7.18 (2H, J=7.74 Hz), 6.78 (s, 1H), 4.82 (d, 2H, J=3.77 Hz), 4.65 (m, 1H), 4.45 (t, 2H, J=6.60 Hz), 4.05 (m), 3.92 (s, 3H), 3.72 (t, 2H), 3.22 (m), 2.65-2.82 (m), 2.28 (m), 1.92 (m, 2H), 1.82 (m), 1.39 (m).

FABMS: 636 (M+H)$^+$.

This compound was prepared according to the method described for the compound 5a by reducing a solution of 4c (720.90 mg, 1.0 mmol) using SnCl$_2$.2H$_2$O (1.12 g, 5.0 mmol). The amino compound 5c obtained was (662 mg, 97% yield). This compound was prepared according to the method described for the compound 6a employing 5c (690.92 mg, 1.0 mmol) and HgCl$_2$ (590 mg, 2.26 mmol), CaCO$_3$ (244 mg, 2.46 mmol) in acetonitrile-water (4:1) to obtain the pure product 6c (318 mg, 58% yield).

$^1$H NMR (CDCl$_3$): δ 8.05 (d, 2H J=7.324 Hz), 7.60 (d, 1H, J=3.66 Hz), 7.32-7.42 (m, 4H, J=8.05 Hz), 4.35 (t, 2H, J=6.5 Hz), 3.92-4.2 (m), 3.90 (s, 3H), 3.42-3.74 (m), 2.29 (t, 2H), 1.74-2.12 (m), 1.6 (m), 1.42 (m, J=7.32 Hz).

FABMS: 482 (M+H)$^+$.

EXAMPLE-4

7-Methoxy-8-[6-(9H-9-carbazolyl)hexyloxy]-(11aS)-1,2,3,11a-tetrahydro-5H-pyrrolo[2,1-c][1,4]-benzodiazepin-5-one 6d This compound was prepared according to the method described for the compound 4a by employing 2S—N-[4-(3-bromopropoxy)-5-methoxy-2-nitrobenzoyl]pyrrolidine-2-carboxaldehyde (1d) diethylthioacetal (521 mg, 1.0 mmol) was added anhydrous potassium carbonate (690 mg, 5.0 mmol) and carbazole (340.37 mg, 1.0 mmol). to obtain the pure product 4d (505 mg, 84% yield).

$^1$H NMR (CDCl$_3$): δ 8.04 (d, 2H, J=7.554 Hz), 7.55 (s, 1H), 7.31-7.41 (m, 4H, J=6.79 Hz), 7.15 (t, 2H, J=6.798 Hz), 6.74 (s, 1H), 4.82 (d, 2H, J=3.77 Hz), 4.67 (m, 1H), 4.32 (t, 2H), 3.99 (t, 2H, J=6.043 Hz), 3.9 (s, 3H), 3.23 (m, 2H, J=6.798 Hz), 2.65-2.84 (m, J=7.554 Hz), 2.26 (m, 1H), 2.1 (m, 1H), 1.92 (m, 4H J=7.554 Hz), 1.82 (m, 4H, J=7.55 Hz), 1.5 (m, 6H), 1.39 (m).

FABMS: 650 (M+H)$^+$.

This compound was prepared according to the method described for the compound 5a by reducing 4d (780.87 mg, 1.0 mmol) using SnCl$_2$.2H$_2$O (1.12 g, 5.0 mmol). The amino compound 5d obtained was (721 mg, 97% yield).

This compound was prepared according to the method described for the compound 6a employing 5d (750 mg, 1.0 mmol) and HgCl$_2$ (582 mg, 2.26 mmol), CaCO$_3$ (230 mg, 2.46 mmol) in acetonitrile-water (4:1) to obtain the pure product 6d (348 mg, 58% yield).).

$^1$H NMR (CDCl$_3$): δ 8.05 (d, 2H, J=8.11 Hz), 7.66 (d, 1H, J=4.427 Hz), 7.38-7.57 (m, 4H), 7.26 (m, 2H), 6.7 (s, 1H), 4.38 (t, 2H, J=6.641 Hz), 4.24 (m), 4.01-4.18 (m), 3.92 (s, 3H), 3.54-3.88 (m), 2.61 (m, 6H), 2.48 (m, 2H), 2.31 (t, 2H), 2.08 (m), 1.92 (m), 1.62 (m), 1.38 (m, 6H), FABMS: 496 (M+H)$^+$.

EXAMPLE-5

7-Methoxy-8-{3-[3,6-di(4-methoxyphenyl)-9H-9-carbazolyl]propoxy}-(11aS)-1,2,3,11a-tetrahydro-5H-pyrrolo[2,1-c][1,4]-benzodiazepin-5-one 10d This compound was prepared according to the method described for the compound 4a by employing 2S—N-[4-(4-bromobutoxy)-5-methoxy-2-nitrobenzoyl]pyrrolidine-2-carboxaldehyde (1a) diethylthioacetal (535 mg, 1.0 mmol) was added anhydrous potassium carbonate (690 mg, 5.0 mmol) and 9-(3-bromopropoxy)-3,6-di(4-methoxyphenyl)-9H-carbazole (7) (340.37 mg, 1.0 mmol). to obtain the pure product 8d (708 mg, 84% yield).

$^1$H NMR (CDCl$_3$): δ 8.21 (s, 2H), 7.56-7.61 (m, 6H, J=8.309 Hz), 7.51 (s, 1H), 7.4 (m, J=8.309 Hz), 6.94 (d, 4H, J=9.065 Hz), 6.82 (s, 1H), 4.82 (d, 1H, J=3.77), 4.62 (m, 1H), 4.05 (s, 3H), 3.85 (s, 6H), 3.04-3.21 (m, 2H), 2.65-2.88 (m, 4H), 2.44 (t, 2H, J=6.043 Hz), 2.23 (m, 1H), 2.04 (m, 1H), 1.64-1.88 (m), 1.48 (m). FABMS: 821 (M+H)$^+$.

This compound was prepared according to the method described for the compound 5a by reducing 8d (794.87 mg, 1.0 mmol) using SnCl$_2$.2H$_2$O (1.12 g, 5.0 mmol). The amino compound 9d obtained was (742 mg, 97% yield).

This compound was prepared according to the method described for the compound 6a employing 9d (764.89 mg, 1.0 mmol) and HgCl$_2$ (582 mg, 2.26 mmol), CaCO$_3$ (230 mg, 2.46 mmol) in acetonitrile-water (4:1) to obtain the pure product 10d (373 mg, 58% yield).

$^1$H NMR (CDCl$_3$): δ 8.25 (s), 7.52-7.68 (m, J=8.309, J=4.532 Hz), 7.49 (d, J=8.309), 7.07 (d, 4H, J=8.309 Hz), 6.58 (s), 4.62 (t, 2H), 4.1 (s, 3H), 3.9 (s, 6H), 3.81 (m, 2H), 3.55 (m,), 2.48 (m), 2.22 (t, 2H), 2.01 (t, 2H), 1.8-1.40 (m).

FABMS: 666 (M+H)$^+$.

EXAMPLE-6

7-Methoxy-8-{4-[3,6-di(4-methoxyphenyl)-9H-9-carbazolyl]butoxy}-(11aS)-1,2,3,11a-tetrahydro-5H-pyrrolo[2,1-c][1,4]-benzodiazepin-5-one 10e This compound was prepared according to the method described for the compound 4a by employing 2S—N-[4-(5-bromopentyloxy)-5-methoxy-2-nitrobenzoyl]pyrrolidine-2-carboxaldehyde (1b) diethylthioacetal (549 mg, 1.0 mmol) was added anhydrous potassium carbonate (690 mg, 5.0 mmol) and 9-(3-bromobutoxy)-3,6-di(4-methoxyphenyl)-9H-carbazole (340.37 mg, 1.0 mmol). to obtain the pure product 8e (719 mg, 84% yield).

$^1$H NMR (CDCl$_3$): δ 8.21 (s, 2H), 7.56-7.61 (m, 6H, J=8.309 Hz), 7.51 (s, 1H), 7.41 (m, J=8.309), 6.94 (d, 4H, J=9.065 Hz), 6.82 (s, 1H), 4.82 (d, 1H, J=3.77 Hz), 4.68 (m, 1H), 4.44 (t, 2H, J=6.79 Hz), 4.02 (m, 2H), 3.92 (s, 3H), 3.85 (s, 6H), 3.21 (m, 2H), 2.65-2.88 (m, 4H), 2.39 (m), 2.23 (m), 1.94 (m), 1.48 (m). FABMS: 835 (M+H)$^+$.

This compound was prepared according to the method described for the compound 5a by reducing 8e (808.87 mg, 1.0 mmol) using SnCl$_2$,2H$_2$O (1.12 g, 5.0 mmol). The amino compound 9e obtained was (755 mg, 97% yield).

This compound was prepared according to the method described for the compound 6a employing 9e (778 mg, 1.0 mmol) and HgCl$_2$ (582 mg, 2.26 mmol), CaCO$_3$ (230 mg, 2.46 mmol) in acetonitrile-water (4:1) to obtain the pure product 10e (381 mg, 58% yield).

$^1$H NMR (CDCl$_3$): δ 8.25 (s), 7.52-7.68 (m, J=8.309, J=4.532 Hz), 7.49 (d, J=8.309 Hz), 7.03 (d, 4H, J=8.309), 6.58 (s, 1H), 4.35 (t, 2H, J=6.59 Hz), 3.92-4.2 (m), 4.02 (m, 2H), 3.92 (s, 3H), 3.85 (s, 6H), 2.61 (m), 2.48 (m), 2.31 (m), 2.08 (m), 1.92 (m), 1.62 (m), 1.38 (m).

FABMS: 680 (M+H)$^+$.

EXAMPLE-7

7-Methoxy-8-(3-{4-[3-(9H-9-carbazoly)propyloxy]piperazino}propyloxy)-(11aS)-1,2,3,11a-tetrahydro-5H-pyrrolo[2,1-c][1,4]benzodiazepin-5-one 14a This compound was prepared according to the method described for the compound 4a by employing (2S)-[N-{4-(3-(piperzin-1-yl)propyloxy)-5-methoxy-2-nitrobenzoyl]pyrrolidine-2-carboxaldehydediethylthioacetal 2a (521 mg, 1.0 mmol) was added anhydrous potassium carbonate (690 mg, 5.0 mmol) and 9-(3-bromophenyl)-9H-carbazole 11a (304 mg, 1.0 mmol). to obtain the pure nitro product 12a (625 mg, 84% yield).

$^1$H NMR (CDCl$_3$): δ 8.04 (d, 2H, J=7.554 Hz), 7.65 (s, 1H), 7.40 (t, 2H, J=8.309 Hz), 7.35 (t, 2H), 7.18 (t, 2H, J=7.743 Hz), 6.78 (s, 1H), 4.84 (d, 2H, J=3.77 Hz), 4.67 (m, 1H), 4.32 (t, 2H, J=6.40 Hz), 3.92 (s, 3H), 3.23 (m, 2H), 2.71-2.89 (m), 2.6 (m, 4H), 2.48 (t, 2H), 2.30 (m), 1.8-2.1 (m), 1.78 (m, 2H), 1.62 (m, 2H), 1.38 (m, 9H).

FABMS: 735 (M+H)$^+$.

This compound was prepared according to the method described for the compound 5b by reducing nitro compound 12a (744 mg, 1.0 mmol) using SnCl$_2$.2H$_2$O (1.12 g, 5.0 mmol). The amino compound 13a obtained was (692 mg, 97% yield). This compound was prepared according to the method described for the compound 6a employing amine 13a (714 mg, 1.0 mmol) and HgCl$_2$ (582 mg, 2.26 mmol), CaCO$_3$ (230 mg, 2.46 mmol) in acetonitrile-water (4:1) to obtain the pure product 14a (346 mg, 58% yield).

$^1$H NMR (CDCl$_3$): δ 8.10 (d, 2H, J=7.324 Hz), 7.64 (d, 1H, J=4.5 Hz), 7.35-7.58 (m, 4H), 7.28 (m, 2H), 6.78 (s, 1H), 4.38 (t, 2H), 4.08 (m, 2H), 3.90 (s, 3H), 3.62-3.84 (m), 3.55 (m), 2.52-2.84 (m), 2.32 (m, 2H), 2.08 (m), 1.62 (m, 2H), 1.23 (m).

FABMS: 580 (M+H)$^+$.

EXAMPLE-8

7-Methoxy-8-(3-{4-[4-(9H-9-carbazoly)butyloxy] piperazino}propyloxy)-(11aS)-1,2,3,11a-tetrahydro-5H-pyrrolo[2,1-c][1,4]benzodiazepin-5-one 14b This compound was prepared according to the method described for the compound 4a by employing (2S)-[N-{4-(3-(piperzin-1-yl)propyloxy)-5-methoxy-2-nitrobenzoyl]pyrrolidine-2-carboxaldehydediethylthioacetal 2a (535 mg, 1.0 mmol) was added anhydrous potassium carbonate (690 mg, 5.0 mmol) and 9-(4-bromobutylphenyl)-9H-carbazole 11b (304 mg, 1.0 mmol). to obtain the pure nitro product 12b (623 mg, 84% yield).

$^1$H NMR (CDCl$_3$): δ 8.04 (d, 2H, J=7.554 Hz), 7.61 (s, 1H), 7.40 (m, 4H, J=7.554 Hz), 7.18 (t, 2H, J=7.554 Hz), 6.78 (s, 1H), 4.84 (d, 1H, J=3.777 Hz), 4.66 (m, 1H), 4.4 (m, 2H, J=6.798 Hz), 3.94 (s, 3H), 3.23 (m, 2H, J=6.798 Hz), 2.68-2.84 (m, 4H, J=6.798 Hz), 2.48 (m, J=7.554), 2.24 (t, 3H, J=6.043 Hz), 1.6-21 (m, J=6.798 Hz), 1.38 (m, 9H, J=6.798 Hz), FABMS: 749 (M+H)$^+$.

This compound was prepared according to the method described for the compound 5a by reducing nitro compound 12b (758 mg, 1.0 mmol) using SnCl$_2$.2H$_2$O (1.12 g, 5.0 mmol). The amino compound 13b obtained was (705 mg, 97% yield).

This compound was prepared according to the method described for the compound 6a employing amine 13b (728 mg, 1.0 mmol) and HgCl$_2$ (582 mg, 2.26 mmol), CaCO$_3$ (230 mg, 2.46 mmol) in acetonitrile-water (4:1) to obtain the pure product 14b (348 mg, 58% yield).).

$^1$H NMR (CDCl$_3$): δ 8.10 (d, 2H, J=7.74 Hz), 7.61 (d, 1H, J=4.532 Hz), 7.35-7.48 (m, 4H), 7.19 (m, 2H), 6.78 (s, 1H), 4.41 (t, 2H, J=6.610 Hz), 4.08 (m, 2H), 3.94 (s, 3H), 3.5-3.8 (m), 3.0 (t, 2H), 2.52 (m), 2.32 (m, 2H), 2.08 (m), 1.62 (m), 1.23 (m).

FABMS: 594 (M+H)$^+$.

EXAMPLE-9

7-Methoxy-8-(4-{4-[3-(9H-9-carbazoly)propyloxy] piperazino}butyloxy)-(11aS)-1,2,3,11a-tetrahydro-5H-pyrrolo[2,1-c][1,4]benzodiazepin-5-one 14c This compound was prepared according to the method described for the compound 4a by employing (2S)-[N-{4-(4-(piperzin-1-yl)butyloxy)-5-methoxy-2-nitrobenzoyl]pyrrolidine-2-carboxaldehydediethylthioacetal 2b (549 mg, 1.0 mmol) was added anhydrous potassium carbonate (690 mg, 5.0 mmol) and 9-(3-bromobutylphenyl)-9H-carbazole 11b (304 mg, 1.0 mmol). to obtain the pure nitro product 12c (623 mg, 84% yield). $^1$H NMR (CDCl$_3$): δ 8.04 (d, 2H, J=7.554 Hz), 7.65 (s, 1H), 7.40 (m, 4H, J=8.309 Hz), 7.18 (t, 2H, J=7.554 Hz), 6.78 (s, 1H), 4.84 (d, 1H, J=3.77 Hz), 4.66 (m, 1H), 4.41 (t, 2H, J=6.043 Hz), 4.15 (m, 2H, J=6.043 Hz), 3.94 (s, 3H), 3.23 (m, 3H, J=6.768 Hz), 2.68-2.89 (m, J=7.98 Hz), 2.59 (m, J=6.798 Hz), 2.48 (m), 2.34 9m), 2.04 (m), 1.84 (m), 1.38 (m, 9H, J=7.552 Hz).

FABMS: 749 (M+H)$^+$.

This compound was prepared according to the method described for the compound 5a by reducing nitro compound 12c (772 mg, 1.0 mmol) using SnCl$_2$.2H$_2$O (1.12 g, 5.0 mmol). The amino compound 13c obtained was (720 mg, 97% yield). This compound was prepared according to the method described for the compound 6a employing amine 13c (742 mg, 1.0 mmol) and HgCl$_2$ (582 mg, 2.26 mmol), CaCO$_3$ (230 mg, 2.46 mmol) in acetonitrile-water (4:1) to obtain the pure product 14c (328 mg, 58% yield).

$^1$H NMR (CDCl$_3$): δ 8.10 (d, 2H, J=7.74 Hz), 7.61 (d, 1H, J=4.532 Hz), 7.35-7.48 (m, 4H), 7.19 (m, 2H), 6.78 (s, 1H), 4.41 (t, 2H, J=6.610 Hz), 4.08 (m, 2H), 3.94 (s, 3H), 3.5-3.8 (m), 3.0 (t, 2H), 2.52 (m), 2.32 (m, 2H), 2.08 (m), 1.62 (m), 1.23 (m).

FABMS: 549 (M+H)$^+$.

EXAMPLE-10

7-Methoxy-8-(4-{-4-[4-(9H-9-carbazoly)butyloxy] piperazino}butyloxy)-(11aS)-1,2,3,11a-tetrahydro-5H-pyrrolo[2,1-c][1,4]benzodiazepin-5-one 14d This compound was prepared according to the method described for the compound 4a by employing (2S)-[N-{4-(4-(piperzin-1-yl)butyloxy)-5-methoxy-2-nitro benzoyl]pyrrolidine-2-carboxaldehyde diethylthioacetal 2b (521 mg, 1.0 mmol) was added anhydrous potassium carbonate (690 mg, 5.0 mmol) and 9-(4-bromobutylphenyl)-9H-carbazole 11b (392 mg, 1.0 mmol). to obtain the pure nitro product 12d, (619 mg, 84% yield).

$^1$H NMR (CDCl$_3$): δ 8.04 (d, 2H, J=7.554 Hz), 7.61 (s, 1H), 7.38 (m, 4H, J=8.309 Hz), 7.18 (t, 2H, J=7.554 Hz), 6.78 (s, 1H), 4.83 (d, 1H, J=3.77 Hz), 4.63 (m, 1H), 4.32 (t, 2H, J=6.043 Hz), 4.09 (t, 2H), 3.94 (s, 3H), 3.22 (m), 2.98 (t, 2H), 2.63-2.88 (m), 2.48 (m), 2.02-2.36 (m), 1.89 (m), 1.52-1.72 (m), 1.38 (m, 9H).

FABMS: 764 (M+H)$^+$.

This compound was prepared according to the method described for the compound 5a by reducing nitro compound 12d (832 mg, 1.0 mmol) using SnCl$_2$.2H$_2$O (1.12 g, 5.0 mmol). The amino compound 13d obtained was (775 mg, 97% yield).

This compound was prepared according to the method described for the compound 6a employing amine 13d (802 mg, 1.0 mmol) and HgCl$_2$ (582 mg, 2.26 mmol), CaCO$_3$ (230 mg, 2.46 mmol) in acetonitrile-water (4:1) to obtain the pure product 14d (385 mg, 58% yield).

$^1$H NMR (CDCl$_3$): δ 8.11 (d, 2H, J=7.524 Hz), 7.68 (d, 1H, J=4.32 Hz), 7.35-7.48 (m, 4H), 7.29 (d, 2H, J=6.78 Hz), 6.78 (s, 1H), 4.34 (t, 2H, J=6.610 Hz), 4.24 (m), 4.1 (m), 3.96 (s, 3H), 3.5-3.8 (m), 2.59, 2.48 (t, 2H), 2.39 (t, 2H), 2.08 (m), 1.9 (m), 1.62 (m), 1.23 (m).

FABMS: 608 (M+H)$^+$.

EXAMPLE-11

7-Methoxy-8-[3-(4-{3-[3,6-di(4-methoxyphenyl)-9H-9-carbazoly]propyloxy}piperazino)proyl]-(11aS)-1,2,3,11a-tetrahydro-5H-pyrrolo[2,1-c][1,4]-benzodiazepin-5-one 18c This compound was prepared according to the method described for the compound 4a by employing (2S)-[N-{4-(3-

(piperzin-1-yl)propyloxy)-5-methoxy-2-nitro benzoyl]pyrrolidine-2-carboxaldehyde diethylthioacetal 2a (535 mg, 1.0 mmol) was added anhydrous potassium carbonate (690 mg, 5.0 mmol) and 9-(3-bromopropyl)-6-di(4-methoxyphenyl)-9H-carbazole 15a (392 mg, 1.0 mmol), to obtain the pure nitro product 16c. (809 mg, 84% yield).

$^1$H NMR (CDCl$_3$): δ 8.21 (s, 2H), 7.48-7.56 (m, 6H, J=9.065 Hz), 7.4 (m, 3H) 6.99 d, 4H, J=9.065 Hz), 6.52 (s, 1H), 4.82 (d, 1H, J=3.77 Hz), 4.68 (m, 1H), 4.42 (t, 2H, J=6.043 Hz), 4.12 (m, 2H), 3.92 (s, 3H), 3.85 (s, 6H), 3.42 (t, 2H), 3.21 (m), 2.81 (m), 2.32-2.61 (m), 2.1 (t, 2H), 1.92 (m), 1.8 (m), 1.43 (m, 8H). FABMS: 947 (M+H)$^+$.

This compound was prepared according to the method described for the compound 5a by reducing nitro compound 16c (846 mg, 1.0 mmol) using SnCl$_2$.2H$_2$O (1.12 g, 5.0 mmol). The amino compound 17c obtained was (794 mg, 97% yield). This compound was prepared according to the method described for the compound 6a employing amine 17c (816 mg, 1.0 mmol) and HgCl$_2$ (582 mg, 2.26 mmol), CaCO$_3$ (230 mg, 2.46 mmol) in acetonitrile-water (4:1) to obtain the pure product 18c (409 mg, 58% yield).

$^1$H NMR (CDCl$_3$): δ 8.21 (s, 2H), 7.52-7.68 (m, J=8.309, J=4.532 Hz), 7.49 (d, J=8.309 Hz), 7.07 (d, 4H, J=8.309), 6.58s, 1H), 4.38 (t, 2H), 4.08 (m, 2H0, 3.90 (s, 3H), 3.62-3.84 (m), 3.55 (m), 2.52-5.84 (m), 2.32 (m, 2H), 2.08 (m), 1.62 (m 2H), 1.23 (m).

FABMS: 793 (M+H).

Biological Activity, of C8-Linked Carbazole-PBD Hybrids:
In Vitro Cytotoxicity

The C8-linked carbazole-PBD hybrids have been tested against sixty human tumour cell lines derived from nine cancer types (leukemia, non-small cell lung cancer, colon cancer, CNS cancer, melanoma, ovarian cancer, renal cancer, prostate cancer and breast cancer) as per NCI protocol, For each compound, dose response curves for individual cell lines have been measured at a minimum of five concentrations at 10 fold dilutions. A protocol of 48 hrs continuous drug exposure has been used, and a sulforhodamine B (SRB) protein assay was used to estimate cell viability or growth. The concentration for 50% cell growth inhibition (GI$_{50}$), total cell growth inhibition (TGI, 0% growth) and 50% cell death (LC$_{50}$, 50% growth) compared with the control has been calculated (Table-3).

Compounds 6c and 14a have been evaluated for in vitro cytotoxicity in sixty cell lines from nine human cancer types of lung (Hop-62, NCI-H226, NCI-H522), leukemia (K-562, SR), colon (HCT-116, HCT-15, HCC-2998), CNS(SF-539), melanoma (SK-MEL-5, UACC-62, M14), ovarian (IGROV1), renal (A498), prostate (PC3) breast (BT-549, MDA-MB-435, HS578T) origin. The results are expressed as percent of cell growth determined relative to that of untreated control cells (Table 1). The representative compounds 6c and 14a has shown significant cytotoxicity against some cancer cell lines.

TABLE 1

Log$_{10}$ GI$_{50}$ (concentration in mol/L) and Log$_{10}$ LC$_{50}$ (concentration in mol/L causing 50% lethality) values for the representative compounds 6c & 14a.

| Cancer | Log$_{10}$ GI$_{50}$ | | Log$_{10}$ LC$_{50}$ | |
|---|---|---|---|---|
| | 6c | 14a | 6c | 14a |
| Leukemia | −5.56 | −7.55 | −4.18 | −4.00 |
| Non small cell lung cancer | −5.64 | −6.96 | −4.78 | −5.62 |
| CNS | −5.76 | −6.96 | −4.97 | −5.67 |

TABLE 1-continued

Log$_{10}$ GI$_{50}$ (concentration in mol/L) and Log$_{10}$ LC$_{50}$ (concentration in mol/L causing 50% lethality) values for the representative compounds 6c & 14a.

| Cancer | Log$_{10}$ GI$_{50}$ | | Log$_{10}$ LC$_{50}$ | |
|---|---|---|---|---|
| | 6c | 14a | 6c | 14a |
| Melanoma | −5.71 | −6.91 | −4.74 | −6.06 |
| Ovarian | −5.57 | −7.22 | −4.59 | −5.80 |
| Renal | −6.39 | −6.72 | −4.99 | −5.61 |
| Prostate | −5.64 | −7.42 | −4.50 | −5.59 |
| Breast | −5.67 | −6.96 | −4.47 | −5.59 |

Each cancer type represents the average of six to eight different cancer cell lines.

The compound 14a exhibits a wide spectrum of activity against sixty cell lines in nine cell panels, with GI$_{50}$ value of <0.01 µM. In the non-small cell lung cancer panel, the growth of HOP-62, NCI-H226, NCI-H522 cell lines were affected by compound 14a with GI$_{50}$ values as 0.08, 0.13 and <0.01 µM respectively. The GI$_{50}$ values of compound 14a against colon cancer COLO 205, HT 29 and SW-620 cell lines are 0.07, 0.05 and 0.04 µM respectively. The GI$_{50}$ values for compound 14a against leukemia HL-60(TB), CCRF-CEM, MOLT-4, and SR cell lines are 0.02, 0.03, 0.02, 0.03 µm respectively. The GI$_{50}$ values for compound 14a against CNS SF-268, U251 cell line is 0.05, 0.03 µM. The GI$_{50}$ values for compound 14a against melanoma LOXIMV1, and M14 cell lines are 0.03, and 0.15 µm respectively. The GI$_{50}$ values for compound 14a against ovarian IGROVI, OVCAR-3 and OVCAR-5 cell line is <0.01, 0.069, 0.03 µM, The GI$_{50}$ values for compound 14a against renal A498 cell line is 0.17 µM. The GI$_{50}$ value for compound 14a against prostate PC-3, DU-145 cell line is 0.03, 0.04 µM. The GI$_{50}$ values for compound 14a against breast MCF-7, MDA-MB-435, and HS 578T cell lines are 0.04, <0.01, and 0.16 µM respectively.

Compounds 6c and 14a exhibit activity against sixty cell lines in nine cancer cell panels with GI$_{50}$ values of 1.03 and <0.01 µM respectively. Compare 6c and 14a, the compound 14a ten folds higher activity than 6c, in vitro cytotoxicity of compounds 6c and 14a in selected cancer cell lines have been illustrated in Table 2. The average GI$_{50}$ values for each cancer panel of compounds 6c and 14a have been illustrated in Table 2.

TABLE 2

In vitro cytotoxicity of compounds 6c and 14a in selected cancer cell lines

| Cancer panel/cell line | GI$_{50}$ (µM) | |
|---|---|---|
| | 6c | 14a |
| Leukemia | | |
| CCRF-CEM | 1.97 | 0.02 |
| HL-60(TB) | 1.72 | 0.03 |
| K-562 | 2.60 | — |
| MOLT-4 | 2.15 | 0.02 |
| Non-small cell lung | | |
| A549/ATCC | 1.57 | — |
| EKVX | 5.27 | 0.14 |
| HOP-62 | 1.80 | 0.08 |
| HOP-92 | 1.31 | 0.27 |
| NCI-H226 | 2.49 | 0.13 |
| Colon | | |
| COLO 205 | 2.11 | 0.07 |
| HCC-2998 | 1.71 | 0.13 |

TABLE 2-continued

In vitro cytotoxicity of compounds 6c
and 14a in selected cancer cell lines

| Cancer panel/cell line | GI$_{50}$ (μM) 6c | 14a |
|---|---|---|
| HCT-116 | 1.65 | 0.06 |
| HCT-15 | 1.67 | 0.28 |
| CNS | | |
| SF-268 | 1.91 | 0.05 |
| SF-539 | 1.85 | 0.12 |
| SNB-19 | 2.05 | 0.21 |
| SNB-75 | 1.05 | 0.15 |
| U251 | 1.59 | 0.03 |
| Melanoma | | |
| LOX IMVI | 2.08 | 0.03 |
| MALME-3M | 2.20 | 0.15 |
| M14 | 2.10 | 0.15 |
| SK-MEL-2 | 1.67 | 0.19 |
| Ovarian | | |
| IGROV1 | 2.08 | <0.01 |
| OVCAR-3 | 1.88 | 0.069 |
| OVCAR-4 | 3.09 | 0.10 |
| OVCAR-5 | 2.42 | 0.03 |
| Renal | | |
| 786-0 | 1.73 | 0.19 |
| A498 | 1.77 | 0.17 |
| ACHN | 1.74 | 0.25 |
| CAKI-1 | 1.93 | 0.12 |
| RXF 393 | 4.34 | 0.22 |
| Breast | | |
| MCF7 | 2.33 | 0.04 |
| MDA-MB- | 2.14 | 0.95 |
| HS 578T | 1.97 | 0.16 |
| MDA-MB-435 | 1.73 | <0.01 |
| Prostate | | |
| PC-3 | 2.36 | 0.03 |
| DU-145 | 2.23 | 0.04 |
| Melanoma | | |
| SK-MEL-28 | 1.80 | 0.06 |
| SK-MEL-5 | 1.73 | 0.23 |
| UACC-257 | 2.29 | 0.15 |
| UACC-62 | 1.86 | 0.15 |

The mean graph mid point values of $\log_{10}$ TGI and $\log_{10}$ LC$_{50}$ as well as $\log_{10}$ GI$_{50}$ for 6c and 14a are listed in Table-3. As demonstrated by mean graph pattern, compounds 6c and 14a exhibit an interesting profile of activity and selectivity for various cell lines. The mean graph mid points of $\log_{10}$ TGI and $\log_{to}$ LC$_{50}$ have shown similar pattern to the $\log_{10}$ GI$_{50}$ mean graph mid points.

TABLE 3

$\log_{10}$ GI$_{50}$, $\log_{10}$ TGI and $\log_{10}$ LC$_{50}$ mean graphs midpoints (MG_MID) of in vitro cytotoxicity data for the compounds 6c and 14a against human tumour cell lines.

| Compound | Log$_{10}$ GI$_{50}$ | Log$_{10}$ TGI | Log$_{10}$ LC$_{50}$ |
|---|---|---|---|
| 6c | −5.67 | −5.29 | −4.67 |
| 14a | −6.96 | −6.24 | −5.57 |

In vitro biological activity studies were carried out at the Advance Center for Treatment Research & Education in Cancer. Compounds 6a, 6b, 6d, 14a, 14d, 10d and 10e exhibits activity against ten cell lines in seven cancer cell panels with GI$_{50}$ values of <2.5 μm. in vitro cytotoxicity of compounds 6a, 6b, 6d, 14a, 14d, and 10d, in selected cancer cell lines has been illustrated in Table 4.

TABLE 4

In vitro cytotoxicity of compounds 6a, 6b, 6d, 14a, 14d, and 10d, in selected cancer cell lines

| Cancer cell line | GI$_{50}$(μM) | | | | | | |
|---|---|---|---|---|---|---|---|
| | 6a | 6b | 6d | 14b | 14d | 10d | 10e |
| Lung | | | | | | | |
| HOP-62 | 1.93 | 1.93 | 1.58 | 0.14 | 1.82 | 0.11 | NT |
| A-549 | NT | NT | NT | NT | NT | 2.10 | NT |
| Oral | | | | | | | |
| KB | 1.87 | 1.87 | 1.95 | 0.14 | 0.15 | 0.18 | NT |
| GURAV | 1.60 | 1.60 | 1.71 | 0.13 | 0.17 | NT | NT |
| Ovary | | | | | | | |
| A-2780 | 1.51 | 1.57 | 1.70 | 0.11 | 0.16 | 0.15 | 2.00 |
| Prostate | | | | | | | |
| PC-3 | NT | NT | NT | NT | NT | 0.16 | 0.16 |
| Cervix | | | | | | | |
| Si-Ha | 1.70 | 1.70 | 1.58 | 0.13 | 0.17 | 0.17 | 0.17 |
| Colon | | | | | | | |
| Colo-205 | 1.68 | 1.70 | 1.62 | 0.14 | 0.16 | 1.70 | 2.9 |
| Breast | | | | | | | |
| Zr-75-1 | 1.89 | 1.81 | 2.14 | 0.15 | 0.15 | | |
| MCF7 | 1.85 | 2.21 | 1.65 | 0.15 | 0.17 | 0.13 | 0.15 |

Carbazole linked pyrrolo[2,1-c][1,4]benzodiazepine hybrids (6c, 14a) as claimed in claims 1-4, wherein the concentration of the compound used for in vitro activity against cancer cell lines for IC$_{50}$ is in the range of 0.16 to 2.33 μM, and <0.01 to 1.24 μM, respectively at an exposure period of at least 48 h.

DNA-Binding Ability of C8-Linked Carbazole-PBD Hybrids
Thermal Denaturation Studies Compounds have been subjected to thermal denaturation studies with duplex-form calf thymus DNA (CT-DNA) using a modification of a reported procedure. Working solutions in aqueous buffer (10 μM NaH$_2$PO$_4$/Na$_2$HPO$_4$, 1 mM Na$_2$EDTA, pH 7.00±0.01) containing CT-DNA (100 μM in phosphate) and the PBD (20 μM) have been prepared by addition of concentrated PBD solutions in DMSO to obtain a fixed [PBD]/[DNA] molar ratio of 1:5. The DNA-PBD solutions have been incubated at 37° C. for 0 and 18 hrs prior to analysis. Samples have been monitored at 260 nm using a Beckman DU-800 spectrophotometer fitted with high performance temperature controller, and heated at 1° C. min$^{-1}$ in the 40-110° C. range. DNA helix→coil transition temperatures (T$_m$) have been obtained from the maxima in the d(A$_{260}$)/dT derivative plots. Drug-induced alterations in DNA melting behavior are given by: □T$_m$=T$_m$(DNA+PBD)-T$_m$(DNA alone), where the T$_m$ value for the PBD-free CT-DNA is 68.5 □0.01. The fixed [PBD]/[DNA] ratio used has not resulted in binding saturation of the host DNA duplex for any compound examined.

The DNA-binding for these C8-linked carbazole-PBD hybrids has been examined by thermal denaturation studies using calf thymus (CT) DNA. Melting studies show that these compounds stabilize the thermal helix→coil or melting stabilization (□T$_m$) for the CT-DNA duplex at pH 7.0, incubated at 37° C., where PBD/DNA molar ratio is 1:5. Data for 6a, 6b, 6c, 14a, 14b, and 14d and DC-81 are included in Table 5 for comparison.

TABLE 5

Thermal denaturation data for carbazole-PBD hybrids with calf thymus (CT) DNA

| PBD hybrids | [PBD]:[DNA] molar ratio[b] | $\Delta T_m$ (°C.)[a] after incubation at 37° C. for 0 h | 18 h |
|---|---|---|---|
| 6a | 1:5 | 4.2 | 5.1 |
| 6b | 1:5 | 4.3 | 4.8 |
| 6c | 1:5 | 4.1 | 4.9 |
| 14a | 1:5 | 7.5 | 8.2 |
| 14b | 1:5 | 7.8 | 8.5 |
| 14d | 1:5 | 7.9 | 8.4 |
| DC-81 | 1:5 | 0.3 | 0.7 |

[a]For CT-DNA alone at pH 7.00 ± 0.01, $T_m$ = 68.5° C. ± 0.01 (mean value from 10 separate determinations), all $\Delta T_m$ values are ± 0.1-0.2° C.
[b]For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].
[c]The $\Delta T_m$ for PBD hybrids 6a, 6b, 6c, 14a, 14b, and 14d at a [PBD]:[DNA] molar ratio of 1:5 increased to a value of 2.0° C., 2.1° C., 2.3° C., 2.0° C., 2.3° C. and 2.1° C. after 18 h incubation respectively.

Significance of the Work Carried Out

The C8-linked carbazole-PBD hybrids that have been synthesized exhibited significant DNA-binding ability and showed cytotoxic activity against fifty-eight human tumour cell lines.

Advantages Of The Invention

1. The present invention provides a new pyrrolo[2,1-c][1,4]benzodiazepine hybrids useful as antitumour agents.
2. It also provides a process for the preparation of pyrrolo[2,1-c][1,4]benzodiazepine hybrids.

Scheme-1

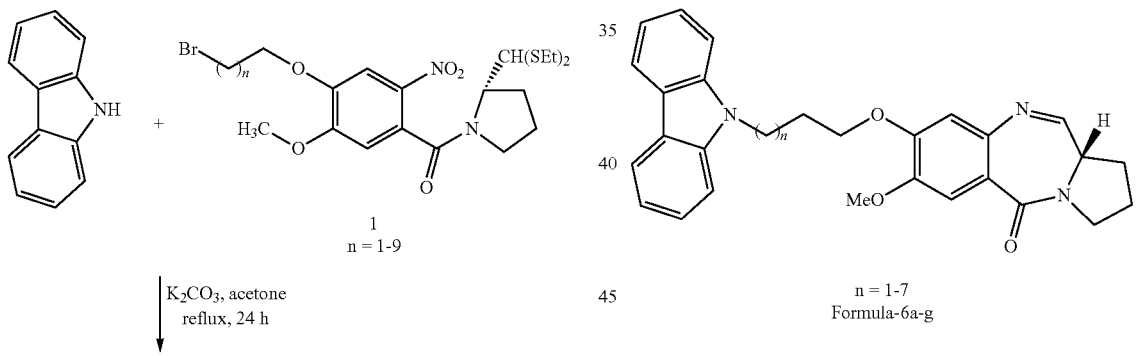

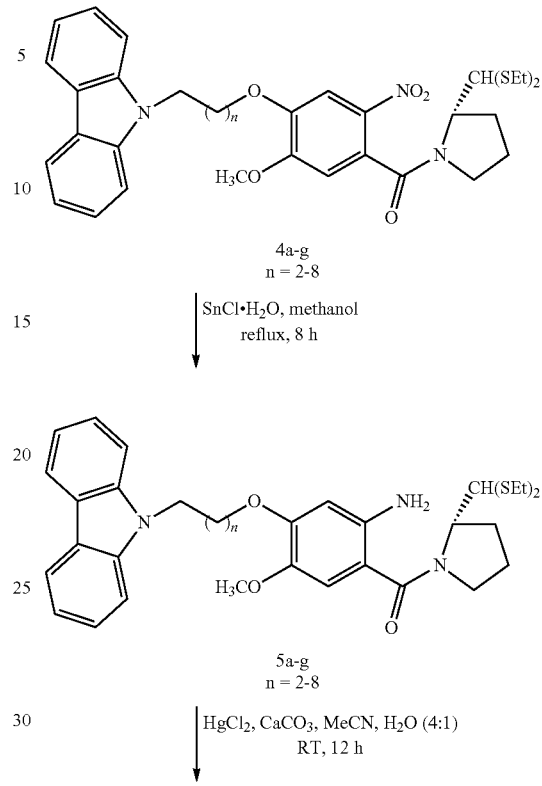

Scheme 2

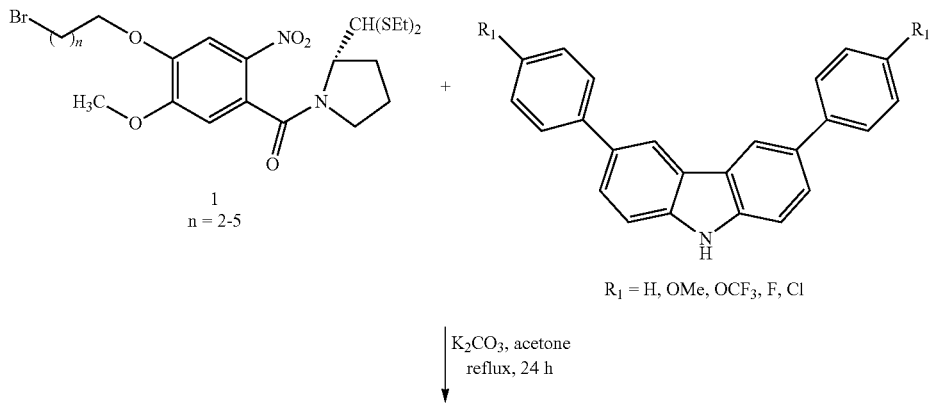

$R_1$ = H, OMe, OCF$_3$, F, Cl

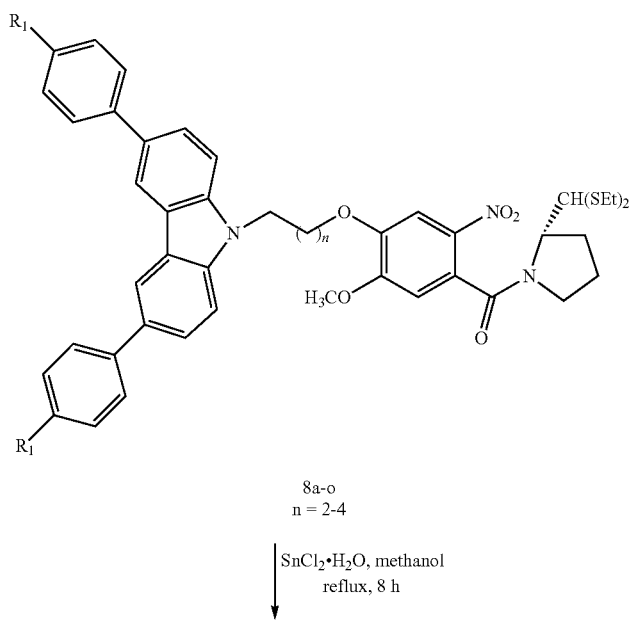
8a-o
n = 2-4
SnCl₂·H₂O, methanol
reflux, 8 h
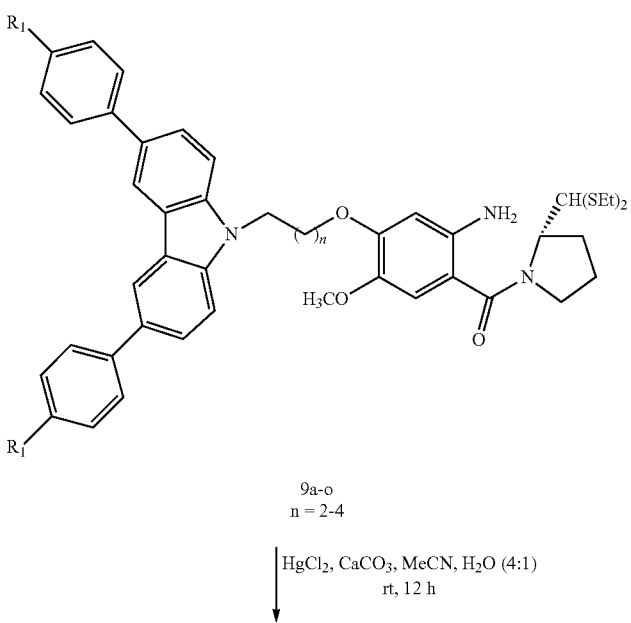
9a-o
n = 2-4
HgCl₂, CaCO₃, MeCN, H₂O (4:1)
rt, 12 h

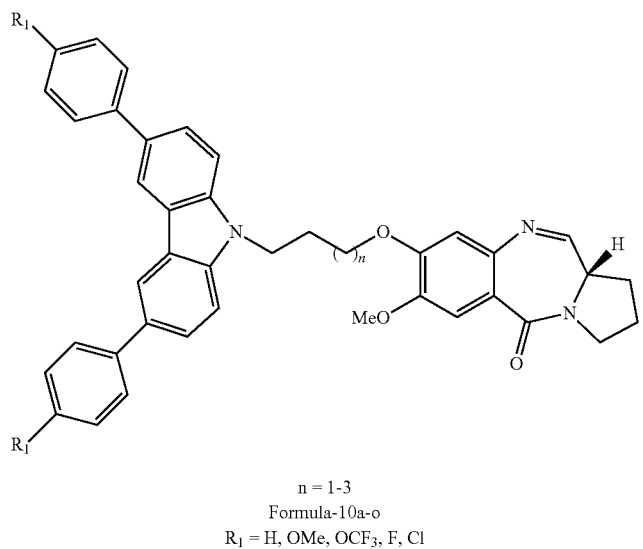
n = 1-3
Formula-10a-o
R₁ = H, OMe, OCF₃, F, Cl
Scheme 3
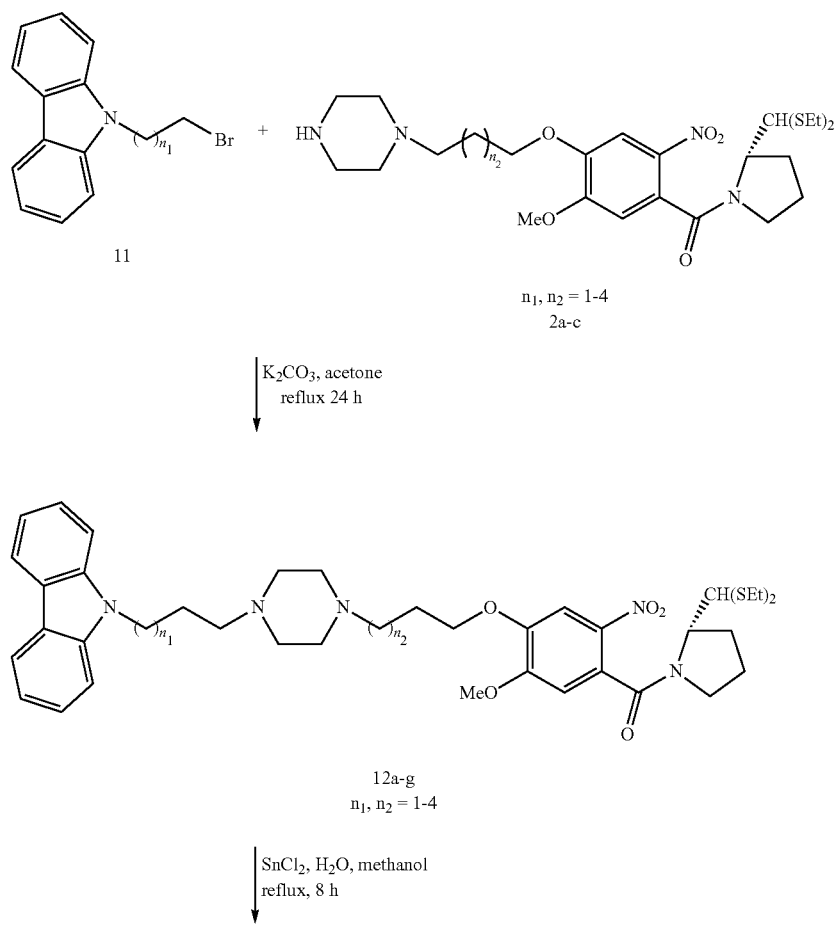

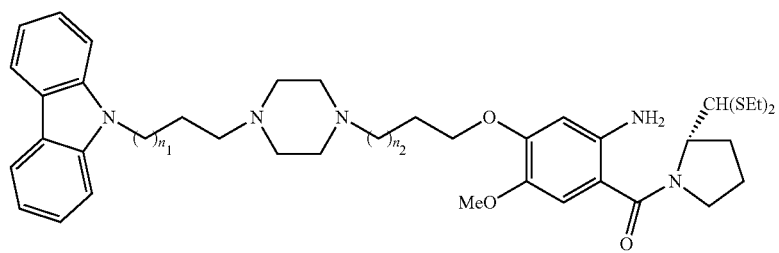
13a-g
$n_1, n_2 = 1-4$
HgCl$_2$, CaCO$_3$, MeCN, H$_2$O (4:1)
rt, 12 h
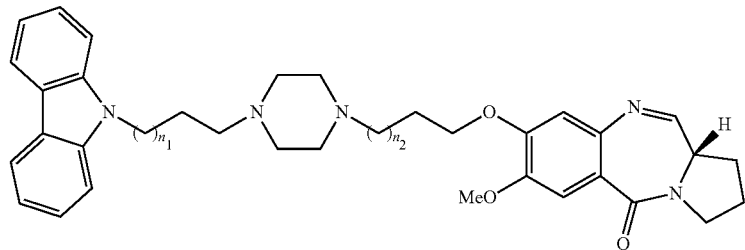
$n_1, n_2 = 1-4$
Formula-14a-g
Scheme 4
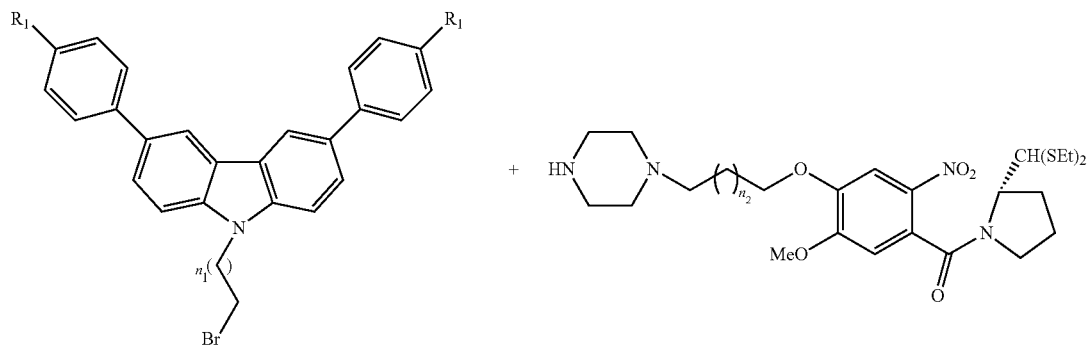
K$_2$CO$_3$, acetone
reflux, 24 h -continued
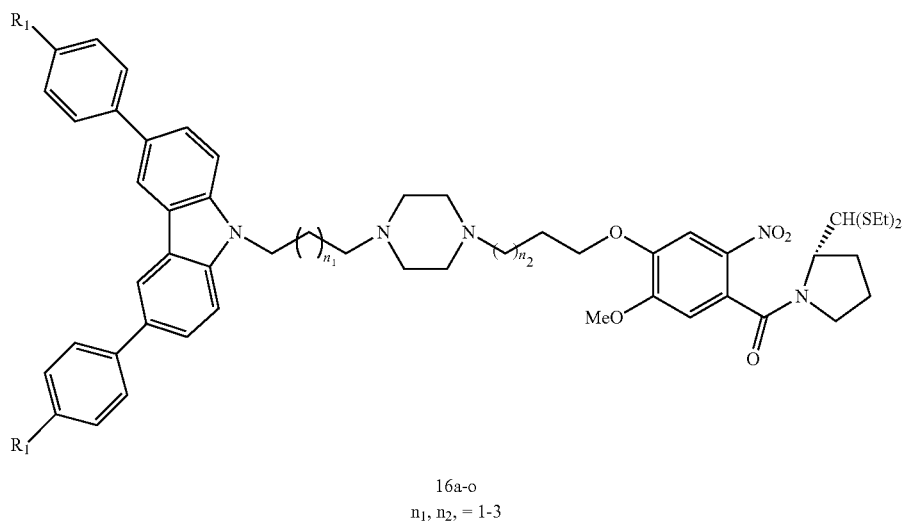
16a-o
$n_1, n_2, = 1-3$
$SnCl_2, H_2O$, methanol
reflux, 8 h
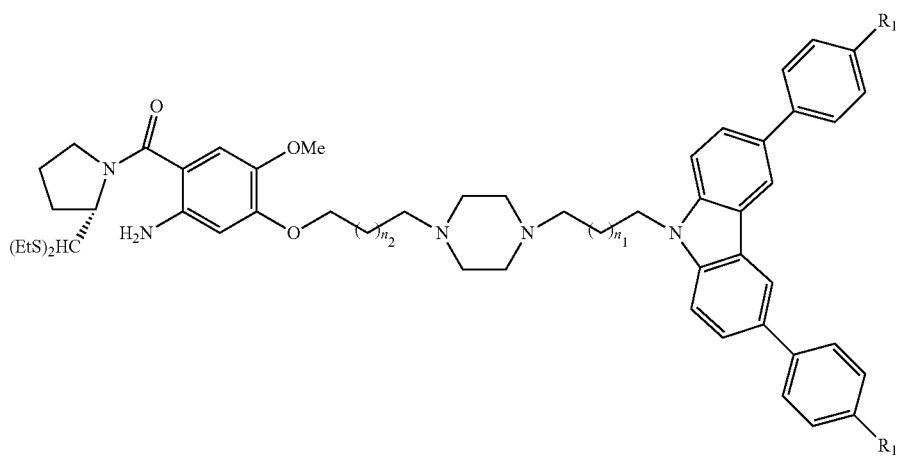
17a-o
$n_1, n_2 = 1-3$
$HgCl_2, CaCO_3$,
MeCN, $H_2O$ (4:1), rt, 12 h

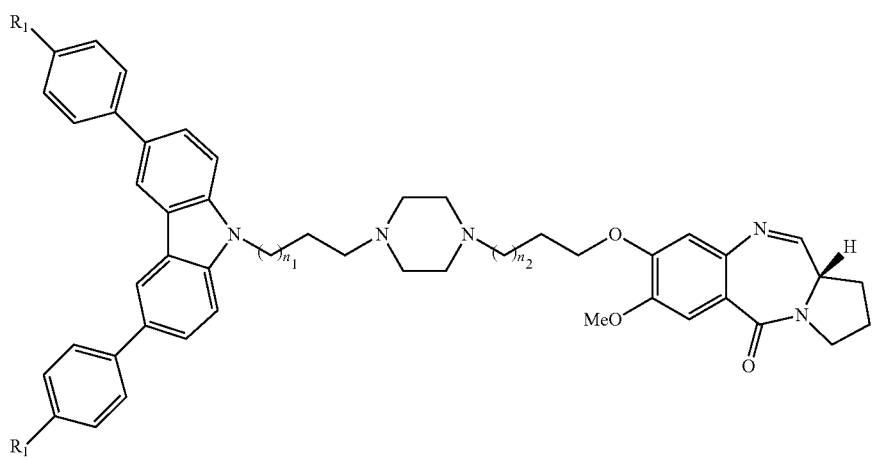

$n_1, n_2 = 1-3$
$R_1 = H, OMe, OCF_3, F, Cl$
Formula 18a-o

We claim:

1. Carbazole linked pyrrolo[2,1-c][1,4]benzodiazepine hybrids of formulae A:

Formula A

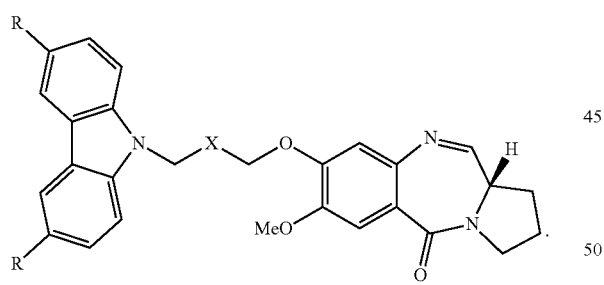

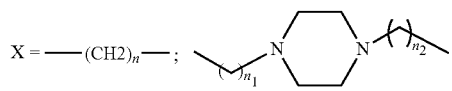

$n = 1-7; n_1, n_2 = 2-6$

R = H, Ph, 4-OMe(Ph), 4-OCF$_3$—(Ph), 4-F(Ph), 4-Cl(Ph)

2. Carbazole linked pyrrolo[2,1-c][1,4]benzodiazepine hybrids as claimed in claim 1, wherein the carbazole linked pyrrolo[2,1-c][1,4]benzodiazepine hybrids of formula A is represented by the compounds of formulae 6a-g, 10a-o, 14a-g and 18a-o:

Formula-6a-g

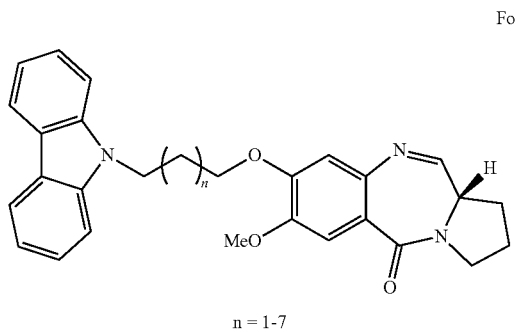

n = 1-7

Formula-10a-o

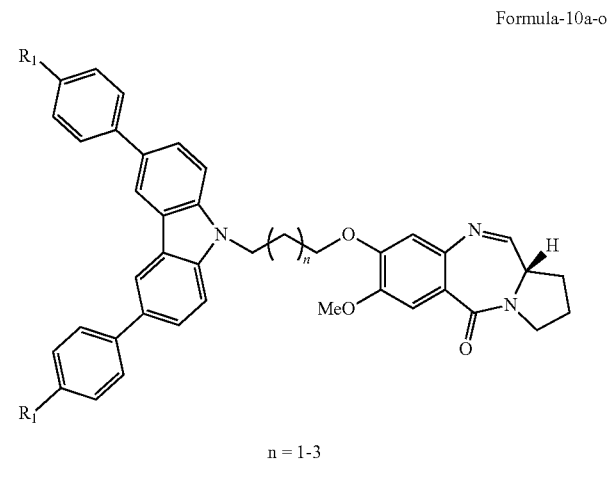

n = 1-3
$R_1$ = H, OMe, $OCF_3$, F, Cl

Formula-14a-g

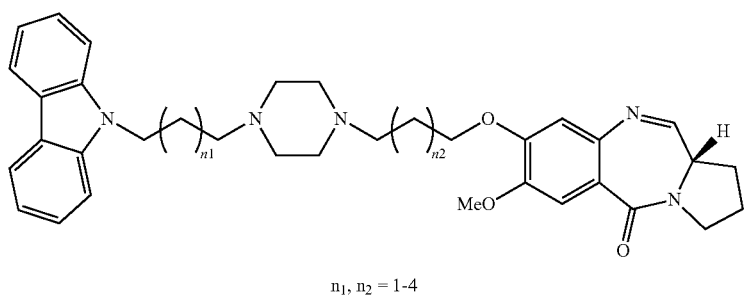

$n_1, n_2$ = 1-4

Formula-18a-o

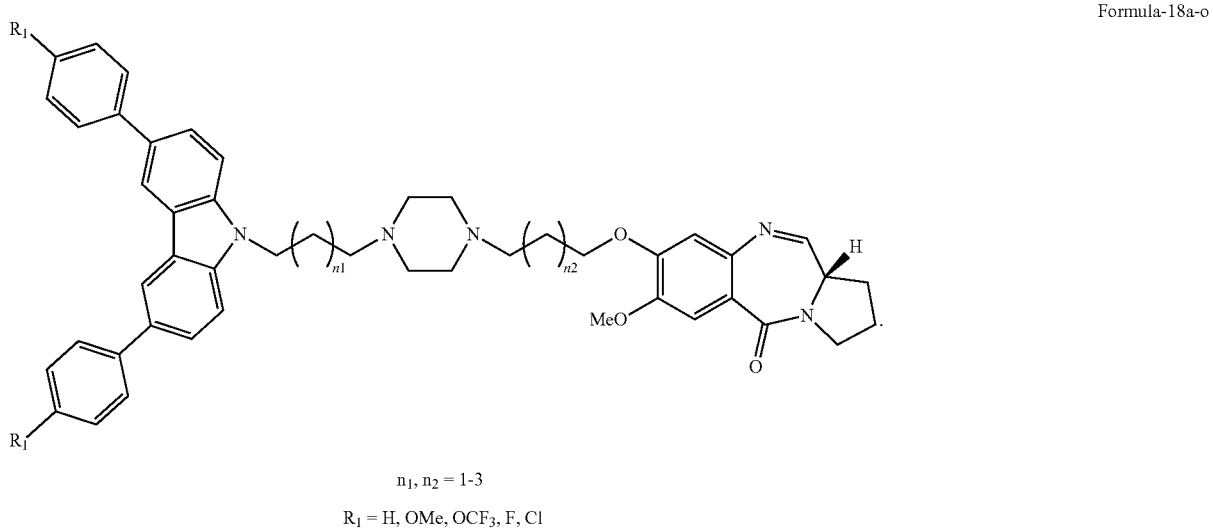

$n_1, n_2$ = 1-3
$R_1$ = H, OMe, $OCF_3$, F, Cl

3. A method for introducing the compounds as claimed in claim 2 into a cell, the method comprising contacting the compounds with the cell, wherein the compounds exhibit in vitro anticancer activity against human cancer cell lines selected from the group consisting of Leukemia Cancer cell lines, CNS cancer cell lines, Melanoma cancer cell lines, Renal cancer cell lines, lung cancer cell lines, breast cancer cell lines, colon cancer cell lines, prostate cancer cell lines and ovarian cancer cell lines.

4. The method as claimed in claim 3, wherein the concentration of the compounds 6a-g and 14a-g used for in vitro activity against leukemia cancer cell lines for $GI_{50}$ is in the range of 1.54 to 2.60, and 0.02 to 0.03 µM respectively at an exposure period of at least 48 hrs, wherein the leukemia cancer cell lines consist of CCRF-CEM, MOLT-4, SR, HL-60 (TB), K-562, RPMI-8226 cell lines.

5. The method as claimed in claim 3, wherein the concentration of the compounds 6a-g and 14a-g used for in vitro activity against ovarian cancer cell lines for $GI_{50}$ is in the range of 1.88 to 4.57, and 0.01 to 0.29 µM respectively at an exposure period of at least 48 hrs, wherein the ovarian cancer cell lines consist of IGROV1, OVCAR-3, OVCAR-4, OVCAR-5, OVCAR-8, and SK-OV-3 cell lines.

6. The method as claimed in claim 3, wherein the concentration of the compounds 6a-g and 14a-g used for in vitro activity against lung cancer cell lines for GI$_{50}$ is in the range of 1.31 to 5.27, and 0.01 to 0.27 μM respectively at an exposure period of at least 48 hrs, wherein the lung cancer cell lines consist of A549/ATCC, EKVX, HOP-62, HOP-92, NCI-H226, NCI-H23, NCI-H322M, NCI-H460, and NCI-H522 cell lines.

7. The method as claimed in claim 3, wherein the concentration of the compounds 6a-g and 14a-g used for in vitro activity against renal cancer cell lines for GI$_{50}$ is in the range of 1.52 to 4.34, and 0.12 to 0.27 μM respectively at an exposure period of at least 48 hrs, wherein the renal cancer cell lines consist of 786-0, A498, ACHN, CAKI-1, RXF 393, SN12C, TK-10, and UO-31 cell lines.

8. The method as claimed in claim 3, wherein the concentration of the compounds 6a-g and 14a-g used for in vitro activity against Colon cancer cell lines for GI$_{50}$ is in the range of 1.65 to 2.11, and 0.04 to 0.28 μM respectively at an exposure period of at least 48 hrs, wherein the Colon cancer cell lines consist of COLO 205, HCC-2998, HCT-116, HCT-15, HT29, KM12, and SW-620 cell lines.

9. The method as claimed in claim 3, wherein the concentration of the compounds 6a-g and 14a-g used for in vitro activity against Breast cancer cell lines for GI$_{50}$ is in the range of 1.73 to 2.79, and 0.01 to 0.95 μM respectively at an exposure period of at least 48 hrs, wherein the Breast cancer cell lines consist of MCF7, MDA-MB-, HS 578T, MDA-MB-435, BT-549, T-47D, and MDA-MB-468 cell lines.

10. The method as claimed in claim 3, wherein the concentration of the compounds 6a-g and 14a-g used for in vitro activity against CNS cancer cell lines for GI$_{50}$ is in the range of 1.05 to 2.05, and 0.03 to 0.21 μM respectively at an exposure period of at least 48 hrs, wherein the CNS cancer cell lines consist of SF-268, SF-539, SNB-19, SNB-75, and U251 cell lines.

11. The method as claimed in claim 3, wherein the concentration of the compounds 6a-g and 14a-g used for in vitro activity against Prostate cancer cell lines for GI$_{50}$ is in the range of 2.23 to 2.36, and 0.03 to 0.04 μM respectively at an exposure period of at least 48 hrs, wherein the Prostate cancer cell lines consist of DU145 and PC3 cell lines.

12. The method as claimed in claim 3, wherein the concentration of the compounds 6a-g and 14a-g used for in vitro activity against Melanoma cancer cell lines for GI$_{50}$ is in the range of 1.67 to 2.29, and 0.03 to 0.23 μM respectively at an exposure period of at least 48 hrs, wherein the Melanoma cancer cell lines consist of LOX IMVI, M14, SK-MEL-5, UACC-257, UACC-62, SK-MEL-28, MALME-3M, and SK-MEL-2 cell lines.

13. The method as claimed in claim 3, wherein the compound 6c exhibits in-vitro cytotoxicity in mean graph midpoint value of −5.67 moles/L, −5.29 moles/L, and −4.67 moles/L for log$_{10}$ GI$_{50}$, log$_{10}$ TGI and log$_{10}$ LC$_{50}$, respectively, against nine human cancer types consisting of leukemia, non-small cell lung cancer, colon cancer, CNS cancer, melanoma, ovarian cancer, renal cancer, prostate cancer and breast cancer.

14. The method as claimed in claim 3, wherein the compound 14a exhibits in-vitro cytotoxicity data in mean graph midpoint value of −6.96 moles/L, −6.24 moles/L, and −5.57 moles/L, for log$_{10}$ GI$_{50}$, log$_{10}$ TGI and log$_{10}$ LC$_{50}$, respectively, against nine human cancer types consisting of leukemia, non-small cell lung cancer, colon cancer, CNS cancer, melanoma, ovarian cancer, renal cancer, prostate cancer and breast cancer.

15. The method as claimed in claim 3, wherein the compound 6a exhibits in-vitro cytotoxicity in breast (MCF-7) GI$_{50}$ (1.85 μmol/L), colon (Colo205) GI$_{50}$ (1.68 μmol/L) and non small cell lung (HOPO62) GI$_{50}$ (1.93 μmol/L) cancer cell lines respectively.

16. The method as claimed in claim 3, wherein the compound 6b exhibits in-vitro cytotoxicity in breast (Zr-75-1) GI$_{50}$ (1.81 μmol/L), colon (Colo 205) GI$_{50}$ (1.70 μmol/L) and non small cell lung (HOPO 62) GI$_{50}$ (1.93 μmol/L) cancer cell lines respectively.

17. The method as claimed in claim 3, wherein the compound 6d exhibits in-vitro cytotoxicity in breast (MCF-7) GI$_{50}$ (1.65 μmol/L), colon (Colo205) GI$_{50}$ (1.62 μmol/L) and non small cell lung (HOPO62) GI$_{50}$ (1.58 μmol/L) cancer cell lines respectively.

18. The method as claimed in claim 3, wherein the compound 14b exhibits in-vitro cytotoxicity in breast (MCF-7) and (Zr-75-1) GI$_{50}$ (0.15 and 0.15 μmol/L), colon (Colo205) GI$_{50}$ (0.14 μmol/L) and non small cell lung (HOPO62) GI$_{50}$ (0.14 μmol/L) cancer cell lines respectively.

19. The method as claimed in claim 3, wherein the compound 14d exhibits in-vitro cytotoxicity in breast (MCF-7) and (Zr-75-1) GI$_{50}$ (0.15 and 0.17 μmol/L), colon (Colo205) GI$_{50}$ (0.16 μmol/L) and oral (KB and GURAV) GI$_{50}$ (0.15 and 0.17 μmol/L) cancer cell lines respectively.

20. The method as claimed in claim 3, wherein the compound 10d exhibits in-vitro cytotoxicity in breast (MCF-7) GI$_{50}$ (0.13 μmol/L), colon (Colo205) GI$_{50}$ (1.70 μmol/L) and non small cell lung (HOPO62) GI$_{50}$ (0.11 μmol/L) cancer cell lines respectively.

21. The method as claimed in claim 3, wherein the compound 10e exhibits in-vitro cytotoxicity in prostate (PC-3) GI$_{50}$(0.16 μmol/L), Cervix (Si-Ha) GI$_{50}$ (0.17 μmol/L) and Breast (MCF-7) GI$_{50}$ (0.15 μmol/L) cancer cell lines respectively.

22. A process for the preparation of carbazole linked pyrrolo[2,1-c][1,4]benzodiazepine hybrids of formulae A:

Formula A

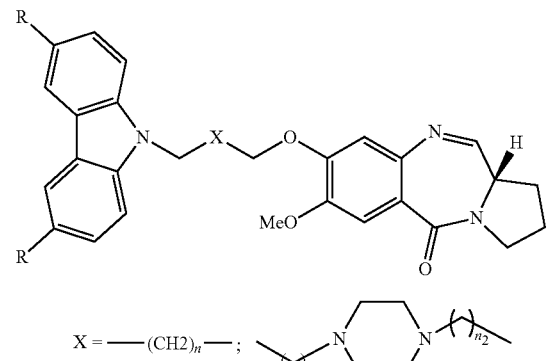

$X = ——(CH_2)_n——$;

$n = 1-6$; $n_1$, $n_2 = 2-6$

R = H, Ph, 4-OMe(Ph), 4-OCF$_3$(Ph), 4-F, 4-Cl the process comprising:
a) adding [5-metboxy-2-nitrobenzoyl)]pyrrolidine-2-carboxaldehydediethylthioacetal of formula 1 or 2 with carbazole of formulae 3, 7, 11, or 15 in mole ratio ranging between 1-1.5 in an organic solvent in the presence of an inorganic base;

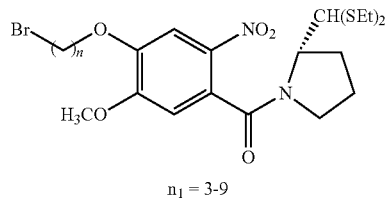

1a-g

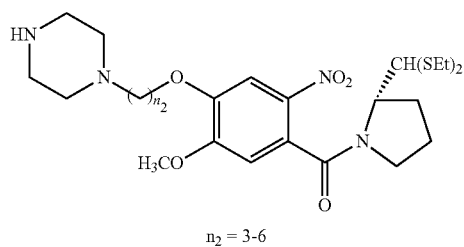

2a-d

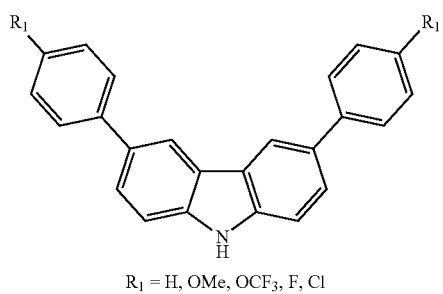

3

R₁ = H, OMe, OCF₃, F, Cl

7

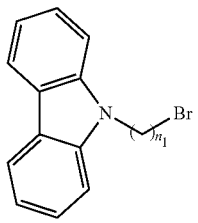

11 n₁ = 3-6

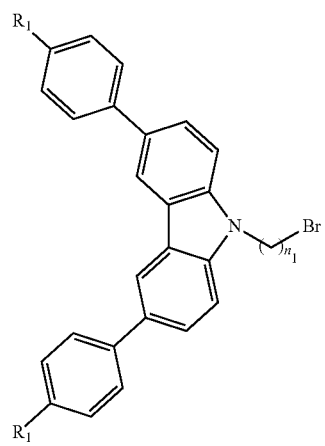

15 n₁ = 3-6
R₁ = H, OMe, OCF₃, F, Cl b) refluxing reaction mixture as obtained in step (a) at temperature ranging between 70-80 °C. for a period of ranging between 24-48 h;
c) removing the inorganic base from the reaction mixture as obtained in step (b) by filtration and evaporating the organic solvent to obtain the resultant crude product;
d) purifying the crude product as obtained in step (c) by column chromatography using ethyl acetate-hexane (1:1) as a solvent system to obtain the desired product of formulae 4a-g, 8a-o, 12a-g and 16a-o;

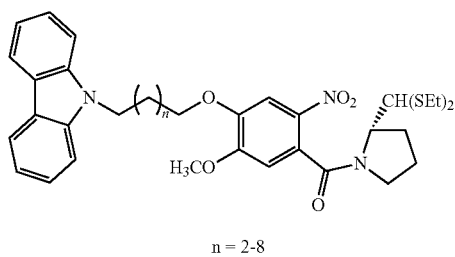

4a-g n = 2-8

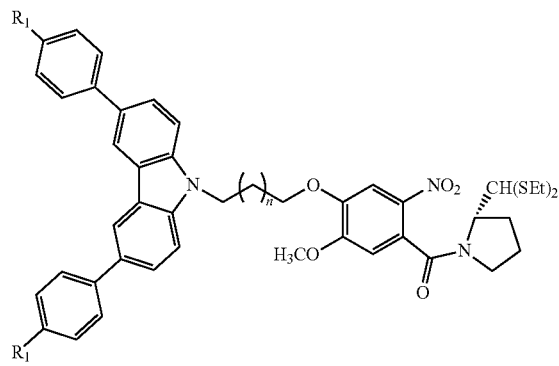

8a-o n = 2-8
R₁ = H, OMe, OCF₃, F, Cl

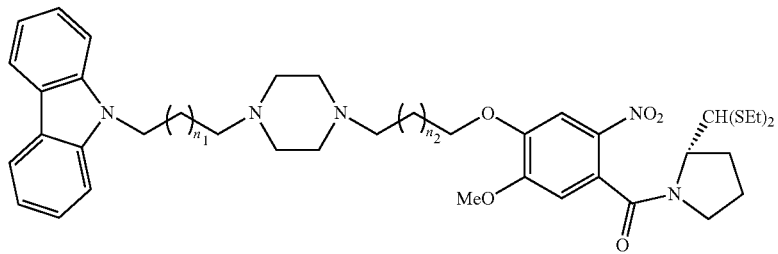

Formula-12a-g $n_1, n_2 = 1-4$

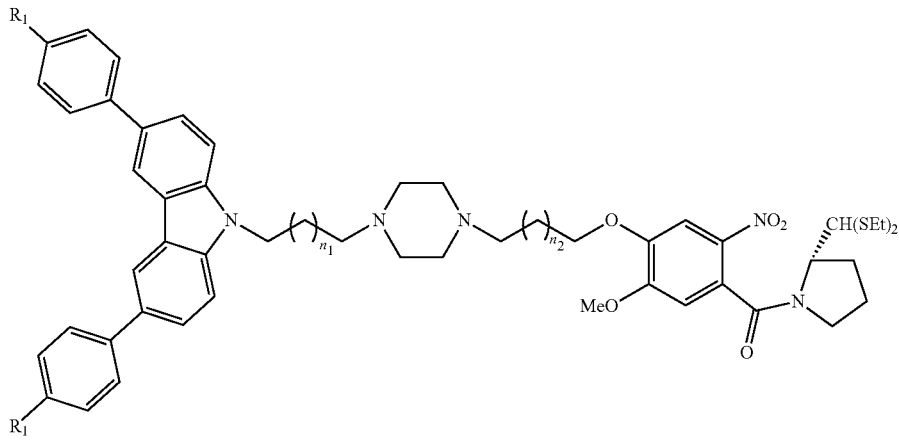

Formula-16a-o $n_1, n_2 = 1-3$
$R_1 = H, OMe, OCF_3, F, Cl$ e) refluxing the compounds of formulae 4a-g, 8a-o, 12a-g and 16a-o as obtained in step (d) with $SnCl_2 \cdot 2H_2O$ in an alcohol to reduce;

f) evaporating the alcohol from reaction mixture as obtained in step (e) and adjusting the pH of the resultant product layer in the range of 7-8 by using a base followed by extraction with ethyl acetate and washing the combined organic phase with brine solution;

g) evaporating the solvent from washed organic phase to obtain the desired products of formulae 5a-g, 9a-o, 13a-g and 17a-o;

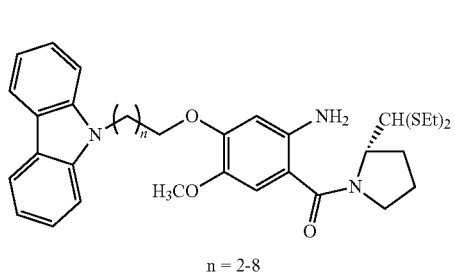

5a-g $n = 2-8$

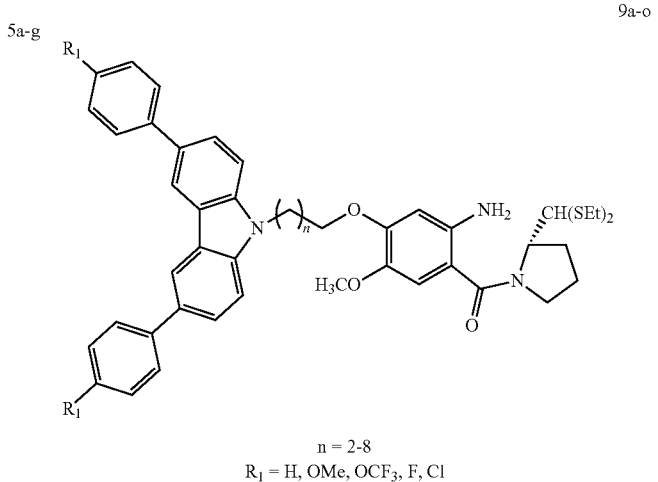

9a-o $n = 2-8$
$R_1 = H, OMe, OCF_3, F, Cl$

-continued

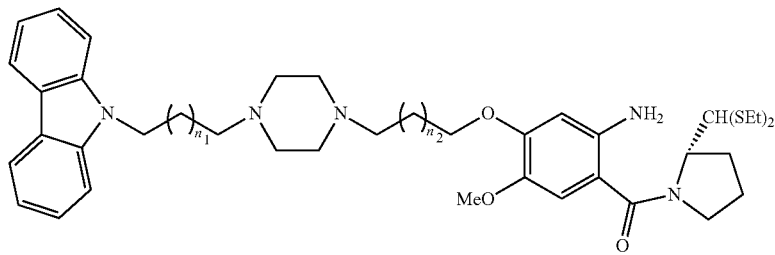

Formula-13a-g n₁, n₂ = 1-4

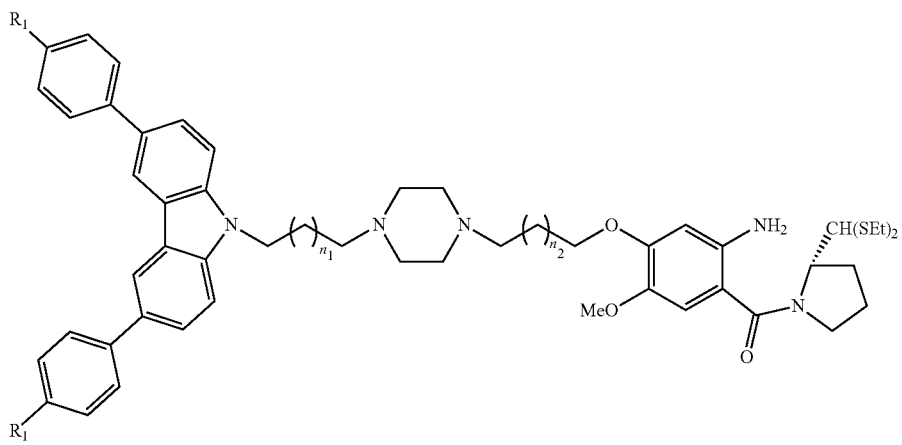

Formula-17a-o n₁, n₂ = 1-3
R₁ = H, OMe, OCF₃, F, Cl h) stirring the compound of formulae 5a-g, 9a-o, 13a-g and 17a-o as obtained in step (g) with $HgCl_2$ and $CaCO_3$ in a solvent preferably acetonitrile:water (4:1) at temperature ranging between 24-27° C. for a period ranging between 12-16 h;

i) extracting the clear organic supernatant from reaction mixture as obtained in step (h) with ethyl acetate and washed with saturated 5% $NaHCO_3$ and brine followed by drying the organic layer over $Na_2SO_4$ to obtain anhydrous organic layer;

j) evaporating the organic solvent from organic layer as obtained in step (i) to obtain white solid;

k) purifying the white solid as obtained in step (j) by column chromatography using ethyl acetate as a solvent system to obtain compounds of formulae 6a-g, 10a-o, 14a-g and 18a-o.

23. A process as claimed in step (a) of claim 22, wherein the organic solvent used is acetone.

24. A process as claimed in step (a) of claim 22, wherein the inorganic base used is potassium carbonate.

25. A process as claimed in step (e) of claim 22, wherein the alcohol used is methanol.

26. A process as claimed in step (f) of claim 22, wherein the base used to adjust pH is 10% $NaHCO_3$.

* * * * *